United States Patent [19]

Bartel et al.

[11] Patent Number: 5,457,104
[45] Date of Patent: Oct. 10, 1995

[54] QUINOLONE- AND NAPHTHYRIDONECARBOXYLIC ACID DERIVATIVES

[75] Inventors: Stephan Bartel, Bergisch Gladbach; Andreas Krebs; Franz Kunisch, both of Odenthal; Uwe Petersen, Leverkusen; Thomas Schenke, Bergisch Gladbach; Klaus Grohe; Michael Schriewer, both of Odenthal; Klaus-Dieter Bremm, Wuppertal; Rainer Endermann, Wuppertal; Karl-Georg Metzger, Wuppertal, all of Germany

[73] Assignee: Bayer Aktiengesellschaft, Leverkusen, Germany

[21] Appl. No.: 180,948

[22] Filed: Jan. 12, 1994

[30] Foreign Application Priority Data

Jan. 19, 1993 [DE] Germany .................. 43 01 246.9

[51] Int. Cl.[6] ................. A61K 31/47; A61K 31/435; C07D 471/04; C07D 215/56
[52] U.S. Cl. ................. 514/234.5; 514/235.2; 514/300; 514/312; 544/127; 544/128; 546/113; 546/123; 546/156; 252/403
[58] Field of Search ................. 546/113, 123, 546/156; 544/127, 128; 514/300, 312, 234.5, 235.2

[56] References Cited

U.S. PATENT DOCUMENTS

| | | | |
|---|---|---|---|
| 4,416,884 | 11/1983 | Ishikawa et al. | 544/361 |
| 4,544,747 | 10/1985 | Ishikawa et al. | 546/156 |
| 4,762,844 | 8/1988 | Grohe et al. | 514/312 |
| 4,804,760 | 2/1989 | Schriewer et al. | 546/153 |
| 4,870,182 | 9/1989 | Schriewer et al. | 546/156 |
| 5,270,340 | 12/1993 | Kunisch et al. | 514/358 |

FOREIGN PATENT DOCUMENTS

| | | |
|---|---|---|
| 0393400 | 10/1990 | European Pat. Off. . |
| 0429304 | 5/1991 | European Pat. Off. . |
| 0520240 | 12/1992 | European Pat. Off. . |
| 0516861 | 12/1992 | European Pat. Off. . |
| 0550903 | 7/1993 | European Pat. Off. . |

OTHER PUBLICATIONS

Journal of Medicinal Chemistry, 35, pp. 198–200 (1992).
J. Am. Chem. Soc. 100, pp. 5179–5185 (1978).
J. Org. Chem. 43, pp. 2164–2167 (1978).
J. Org. Chem. 40, pp. 24–28 (1975).
Houben–Weyl, Methoden der Org. Chemie, Bd. E4, pp. 144–149 (1983).
JFW McOmie, Protective Groups In Org. Chemistry (1973), p. 43.
P. A. Grieco et al., Tetrahedreon 42, pp. 2847–2853 (1986).
JP 1,308,281 (Abstract) (1990).
Helvetica Chimica Acta 59, pp. 222–229 (1976).
JP 3,291,258 (Abstract) (1991).
Japanese Abstract 1,308,281, Dain, Pharmaceuticals, p. 14, Week 9004 (1990).

*Primary Examiner*—Bernard Dentz
*Attorney, Agent, or Firm*—Sprung Horn Kramer & Woods

[57] ABSTRACT

The invention relates to new quinolone- and naphthyridonecarboxylic acid derivatives which have hydrogen in the 6-position, to processes for their preparation, and to antibacterial compositions and feed additives containing them.

7 Claims, No Drawings

QUINOLONE- AND NAPHTHYRIDONECARBOXYLIC ACID DERIVATIVES

The invention relates to new quinolone- and naphthyridonecarboxylic acid derivatives which have hydrogen in the 6-position, to processes for their preparation, and to antibacterial compositions and feed additives containing them.

It has already been disclosed that such quinolonecarboxylic acids have antibacterial activity. Examples can be found in U.S. Pat. No. 4,416,884, EP-A 393,400. 8-Methyl-7-piperazinylquinolonecarboxylic acids were described in DE-A 3,007,006, and 7-(3-aminopyrrolidinyl)-8-fluoroquinolonecarboxylic acids in Journal of Medicinal Chemistry 35, 198 (1992). Compounds of the general formula (I)

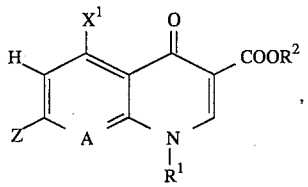

in which
R$^1$ represents straight-chain or branched C$_1$–C$_4$-alkyl which is optionally substituted by hydroxyl, halogen or C$_1$–C$_3$-alkoxy, C$_3$–C$_6$-cycloalkyl which is optionally substituted by C$_1$–C$_3$-alkyl or halogen, or C$_2$–C$_4$-alkenyl, furthermore C$_1$–C$_3$-alkoxy, amino, monoalkylamino having 1 to 3 C atoms, dialkylamino having 1 to 3 C atoms per alkyl group, or phenyl which is optionally monosubstituted to trisubstituted by halogen, R$^2$ represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)-methyl, X$^1$ represents hydrogen, halogen, amino, methyl or trifluoromethyl, Z represents radicals of the structures

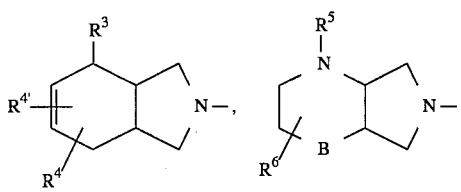

in which
R$^3$ represents hydrogen, hydroxyl, —NR$_7$R$_8$, hydroxymethyl or —CH$_2$—NR$^7$R$^8$, in which
R$^7$ denotes hydrogen, C$_1$–C$_3$-alkyl which is optionally substituted by hydroxyl, or denotes alkoxycarbonyl having 1 to 4 C atoms in the alkoxy moiety, or C$_1$–C$_3$-acyl, and
R$^8$ denotes hydrogen or methyl, R$^4$ represents hydrogen, straight-chain or branched C$_1$–C$_3$-alkyl or cyclopropyl, R$^{4'}$ represents hydrogen or methyl, R$^5$ represents hydrogen or methyl, R$^6$ represents hydrogen, methyl or radicals of the structures —CH=CH—CO$_2$R$^{5'}$, —CH$_2$—CH$_2$—CO$_2$R$^{5'}$, —CH$_2$—CO—CH$_3$, —CH$_2$—CH$_2$—CN, R$^{5'}$ represents methyl or ethyl, B represents —CH$_2$—, O or a direct bond and A represents N or C—R$^9$, in which
R$^9$ represents H, halogen, methyl, trifluoromethyl, vinyl, ethinyl, hydroxyl or methoxy, or else together with R$^1$ can form a bridge of the structure

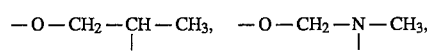

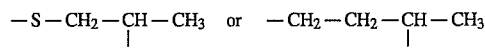

have now been found in the form of racemates or as enantiomerically pure compounds, their pharmaceutically utilizable hydrates and acid addition salts and the alkali metal salts, alkaline earth metal salts, silver salts and guanidinium salts of the carboxylic acids on which they are based. In comparison with known representatives of this structural type, the compounds according to the invention have a more powerful antibacterial activity, in particular in the Gram-positive sector.

They are therefore suitable as active compounds for human and veterinary medicine, veterinary medicine also including the treatment of fish for the therapy or prevention of bacterial infections.

Preferred compounds of the formula (I) are those in which
R$^1$ represents C$_1$–C$_2$-alkyl which is optionally substituted by hydroxyl or fluorine, C$_3$–C$_5$-cycloalkyl which is optionally substituted by fluorine, or vinyl, amino, monoalkylamino having 1 to 2 C atoms, dialkylamino having 1 to 2 C atoms per alkyl group, or phenyl which is optionally monosubstituted to disubstituted by halogen, R$^2$ represents hydrogen, alkyl having 1 to 2 carbon atoms which is optionally substituted by amino or dimethylamino, or (5-methyl-2-oxo-1,3-dioxol-4-yl)methyl, X$^1$ represents hydrogen, fluorine, chlorine, trifluoromethyl or amino, Z represents radicals of the structures

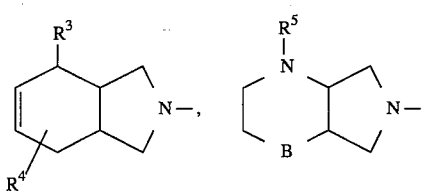

in which
R$^3$ represents hydrogen, hydroxyl, —NR$^7$R$^8$, hydroxymethyl or —CH$_2$——NR$^7$R$^8$, in which
R$^7$ denotes hydrogen, C$_1$–C$_2$-alkyl which is optionally substituted by hydroxyl, or denotes alkoxycarbonyl having 1 to 4 C atoms in the alkoxymoiety, or C$_1$–C$_3$-acyl, and
R$^8$ denotes hydrogen or methyl, R$^4$ represents hydrogen, straight-chain or branched C$_1$–C$_3$-alkyl or cyclopropyl, R$^5$ represents hydrogen or methyl, B represents —CH$_2$—, O or a direct bond and A represents N or C-R$^9$, in which
R$^9$ represents H, chlorine, fluorine, methyl, trifluoromethyl, hydroxyl or methoxy, or else together with $R^1$ can form a bridge of the structure

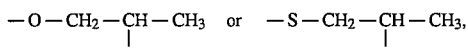

and their pharmaceutically utilizable hydrates and acid addition salts and the alkali metal salts, alkaline earth metal salts, silver salts and guanidinium salts of the carboxylic acids on which they are based.

Particularly preferred compounds of the formula (I) are those in which $R^1$ represents methyl, ethyl, cyclopropyl which is optionally substituted by fluorine, or phenyl which is optionally monosubstituted or disubstituted by fluorine, $R^2$ represents hydrogen, methyl or ethyl, $X^1$ represents hydrogen, fluorine, trifluoromethyl or amino, Z represents radicals of the structures

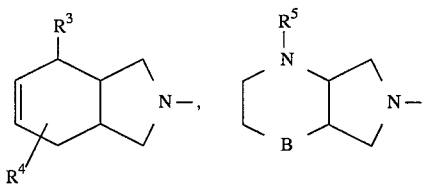

in which $R^3$ represents hydrogen, hydroxyl, $-NR^7R^8$, hydroxymethyl or $-CH_2-NR^7R^8$, in which $R^7$ denotes hydrogen, methyl, alkoxycarbonyl having 1 to 4 C atoms in the alkoxy moiety, or $C_1-C_3$-acyl, and $R^8$ denotes hydrogen or methyl, $R^4$ represents hydrogen, straight-chain or branched $C_1-C_3$-alkyl or cyclopropyl, $R^5$ represents hydrogen or methyl, B represents $-CH_2-$, O or a direct bond and A represents N or $C-R^9$, in which $R^9$ represents H, chlorine, fluorine, methyl, methoxy, trifluoromethyl, or else together with $R^1$ can form a bridge of the structure

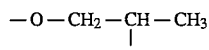

and their pharmaceutically utilizable hydrates and acid addition salts and the alkali metal salts, alkaline earth metal salts, silver salts and guanidinium salts of the carboxylic acids on which they are based.

Furthermore, it has been found that compounds of the formula (I) are obtained when compounds of the formula (II)

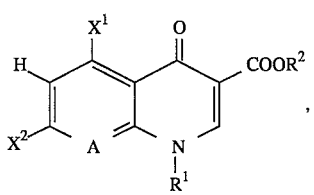

in which $R^1$ $R^2$, $X^1$ and A have the abovementioned meanings and $X^2$ represents halogen, in particular fluorine or chlorine, are reacted with compounds of the formula (III), $$Z-H \qquad (III),$$

in which

Z has the abovementioned meaning, if appropriate in the presence of acid scavengers.

If, for example, 1-cyclopropyl-7,8-difluoro-1,4-dihydro-4-oxo-3-quinolinecarboxylic acid and 4-methylamino-1,3,3a,4,7,7a-hexahydroisoindole are used, the course of the reaction can be represented by the following equation:

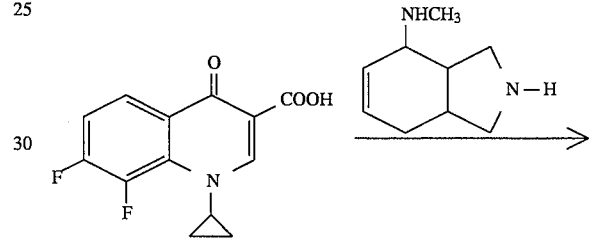

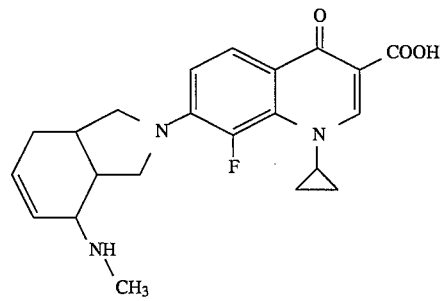

The compounds of the formula (II) which are used as starting compounds are known or can be prepared by known processes. If appropriate, they can be employed as racemates, enantiomers or pure diastereomers.

The following may be mentioned as examples:

1-cyclopropyl-7,8-difluoro-1,4-dihydro-4-oxo-3-quinolinecarboxylic acid, 7-chloro-1-cyclopropyl-1,4-dihydro-4-oxo-3-quinolinecarboxylic acid, 7-chloro-1-ethyl-8-fluoro-1,4-dihydro-4-oxo-3-quinolinecarboxylic acid, 1-ethyl-7-fluoro-1,4-dihydro-4-oxo-3-quinolinecarboxylic acid, ethyl 7-chloro-1-ethyl-1,4-dihydro-4-oxo-3-quinolinecarboxylic acid, 7,8-dichloro-1-ethyl-1,4-dihydro-4-oxo-3-quinolinecarboxylic acid, 1-ethyl-7-fluoro-8-methyl-1,4-dihydro-4-oxo-3-quinolinecarboxylic acid, ethyl 7-chloro-1-(4-fluorophenyl)-1,4-dihydro-5-methyl-4-oxo- 1,8-naphthyridine-3-carboxylate, ethyl 8-chloro-1-chloropropyl-5,7-difluoro-1,4-dihydro-4-oxo-3-quinolinecarboxylate,
ethyl 5-amino-1-cyclopropyl-7,8-difluoro-1,4-dihydro-4-oxo- 3-quinolinecarboxylate,
ethyl 1-cyclopropyl-5,7,8-trifluoro-1,4-dihydro-4-oxo-3-quinolinecarboxylate,
1-cyclopropyl-7-fluoro-1,4-dihydro-8-methyl-4-oxo-3-quinolinecarboxylic acid,
1-cyclopropyl-7,8-difluoro-1,4-dihydro-5-methyl-4-oxo-3-quinolinecarboxylic acid,
5-bromo-1-cyclopropyl-7,8-difluoro-1,4-dihydro-4-oxo-3-quinolinecarboxylic acid,
5-chloro-1-cyclopropyl-7,8-difluoro-1,4-dihydro-4-oxo-3-quinolinecarboxylic acid,
1-cyclopropyl-7-fluoro-1,4-dihydro-8-methoxy-4-oxo-3-quinolinecarboxylic acid,
7,8-difluoro-1-(2,4-difluorophenyl)-1,4-dihydro-4-oxo-3-quinolinecarboxylic acid,
8-chloro-7-fluoro-1-(2,4-difluorophenyl)-1,4-dihydro-4-oxo-3-quinolinecarboxylic acid,
7-fluoro-1-(2,4-difluorophenyl)-1,4-dihydro-4-oxo-3-quinolinecarboxylic acid,
10-fluoro-2,3-dihydro-3-methyl-7-oxo-7H-Pyrido[1,2,3-d,e][1,4]benzoxazine-6-carboxylic acid,
10-chloro-2,3-dihydro-3-methyl-7-oxo-7H-Pyrido[1,2,3-d,e][1,4]benzoxazine-6-carboxylic acid,
10-chloro-8-fluoro-2,3-dihydro-3-methyl-7-oxo-7H-pyrido[1,2,3-d,e][1,4]benzoxazine-6-carboxylic acid,
10-chloro-2,3-dihydro-3-methyl-8-nitro-7-oxo-7H-pyrido[1,2,3-d,e][1,4]benzoxazine-6-carboxylic acid,
10-chloro-2,3-dihydro-3,8-dimethyl-7-oxo-7H-Pyrido[1,2,3-d,e][1,4]benzoxazine-6-carboxylic acid,
8-chloro-6,7-dihydro-1-oxo-1H,5H-benzo[ij]quinolizine-2-carboxylic acid,
8-chloro-1-cyclopropyl-7-fluoro-1,4-dihydro-4-oxo-3-quinolinecarboxylic acid,
7,8-difluoro-1-(2-fluorocyclopropyl)-1,4-dihydro-4-oxo-3-quinolinecarboxylic acid,
8-chloro-7-fluoro-1-(2-fluorocyclopropyl)-1,4-dihydro-4-oxo-3-quinolinecarboxylic acid,
1-cyclopropyl-7,8-difluoro-5-trifluoromethyl-1,4-dihydro-4-oxo-3-quinolinecarboxylic acid,
-cyclopropyl-5,7-difluoro-8-trifluoromethyl-1,4-dihydro-4-oxo-3-quinolinecarboxylic acid,
7-chloro-1-cyclopropyl-1,4-dihydro-4-oxo-1,8-naphthyridine-3-carboxylic acid, and
7-chloro-1-(2,4-difluorophenyl)-1,4-dihydro-4-oxo-1,8-naphthyridine-3-carboxylic acid.

Some of the amines of the formula (III) used as starting compounds are known. Chiral amines can be employed as racemates or as enantiomerically pure or diastereomerically pure compounds.

The following may be mentioned as examples:
2,7-diazabicyclo[3.3.0]octane,
2,8-diazabicyclo[4.3.0]nonane,
2-methyl-2,8-diazabicyclo[4.3.0]nonane,
2-oxa-5,8-diazabicyclo[4.3.0]nonane,
5-methyl-2-oxa-5,8-diazabicyclo[4.3.0]nonane,
4-amino-1,3,3a,4,7,7a-hexahydroisoindole,
4-methylamino-1,3,3a,4,7,7a-hexahydroisoindole,
5-methyl-4-methylamino-1,3,3a,4,7,7a-hexahydroisoindole,
7-methyl-4-methylamino-1,3,3a,4,7,7a-hexahydroisoindole,
7a-methyl-4-methylamino-1,3,3a,4,7,7a-hexahydroisoindole,
6,7-dimethyl-4-methylamino-1,3,3a,4,7,7a-hexahydroisoindole,
4-dimethylamino-1,3,3a,4,7,7a-hexahydroisoindole,
4-ethylamino-1,3,3a,4,7,7a-hexahydroisoindole,
4-aminoethyl-1,3,3a,4,7,7a-hexahydroisoindole,
4-methylaminomethyl-1,3,3a,4,7,7a-hexahydroisoindole,
4-hydroxy-1,3,3a,4,7,7a-hexahydroisoindole,
7-isopropyl-4-methylamino-1,3,3a,4,7,7a-hexahydroisoindole,
4-amino-7-isopropyl-1,3,3a,4,7,7a-hexahydroisoindole,
4-hydroxymethyl-1,3,3a,4,7,7a-hexahydroisoindole,
4-amino-7-cyclopropyl-1,3,3a,4,7,7a-hexahydroisoindole, Most of the substituted 1,3,3a,4,7,7a-hexahydroisoindoles are new. They can be obtained, for example, by Diels-Alder reaction of dienes of the formula (1)

in which $R^4$ has the abovementioned meaning and $R^{10}$ is either identical to $R^3$ or denotes a functional group which can be converted into $R^3$, with dienophiles of the formula (2),

in which $R^{11}$ denotes hydrogen or a protective group such as trimethylsilyl, benzyl, $C_1$–$C_4$-alkylphenylmethyl, methoxybenzyl or benzylhydryl, followed by reduction of the carbonyl groups and, if appropriate, elimination of the protective group.

Suitable diluents for the Diels-Alder reaction are all inert organic solvents. These preferably include ethers, such as diisopropyl ether, di-n-butyl ether, dimethoxyethane, tetrahydrofuran and anisole, hydrocarbons, such as, for example, hexane, methylcyclohexane, toluene, xylene and mesitylene, and halogenated hydrocarbons, such as, for example, chloroform, 1,2-dichloroethane and chlorobenzene. However, the Diels-Alder reaction can also be carried out without solvents.

The reaction temperatures can be varied within a substantial range. In general, the process is carried out between approximately −20° C. and +200° C., preferably between −20° C. and +150° C. The Diels-Alder reaction is usually carried out under atmospheric pressure. To accelerate the reaction, however, it is also possible to use pressures up to 1.5 GPa.

The carbonyl groups can be reduced using complex hydrides. Hydrides which can be employed are, for example, lithium aluminiumhydride, lithium borohydride, lithium triethylborohydride, sodium-bis-[2-methoxyethoxyethoxy]-aluminium hydride or sodium borohydride in the presence of Lewis acid catalysts, such as chlorotrimethylsilane, boron trifluoride etherate or aluminium chloride.

Diluents which can be employed are ethers, such as, for example, diethyl ether, tetrahydrofuran, dioxane or dimethoxyethane, and hydrocarbons, such as, for example, hexane, methylcyclohexane and toluene, or else mixtures of these.

The reaction temperatures can be varied in a range of between −40° and +180° C., preferably between 0° and 140°

C. In general, the reduction is carried out under atmospheric pressure, but it can also be carried out under reduced pressure or under superatmospheric pressure.

It is recommended to use pressures between 100 and 1000 kPa to achieve higher reaction temperatures using low-boiling solvents.

The complex hydrides are at least employed in an amount corresponding to the stoichiometry of the reduction. However, an excess, preferably between 30 and 300%, is generally employed.

A protective group which may be present is eliminated by the generally known methods of protective group chemistry (cf., for example, T. W. Greene, "Protective Groups in Organic Synthesis", John Wiley & Sons, New York 1981).

The starting substances of the formulae (1) and (2) are known or can be prepared by generally known methods of organic chemistry [cf., for example, J. Am. Chem. Soc. 100, 5179 (1978), J. Org. Chem. 43, 2164 (1978), DE 3,927,115, J. Org. Chem. 40, 24 (1975)].

If, for example, 1-(tert.-butyloxycarbonylamino)-1,3-butadiene and maleimide are used as starting materials and lithium aluminium hydride as reducing agent, the course of the reaction can be represented by the following equation:

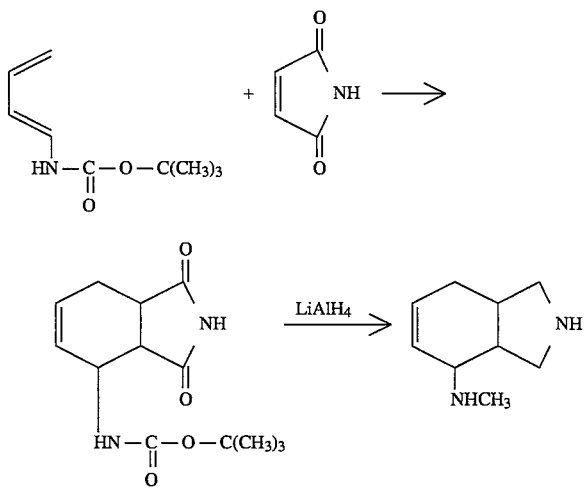

In a particular embodiment of the preparation process, all steps can be carried out without isolation of the intermediates if a suitable solvent, such as, for example, tetrahydrofuran, is used. If, for example, 1-(tert.-butyloxycarbonylamino)-1,3-pentadiene and N-trimethylsilyl-maleimide are used as starting materials, the course of the reaction can be represented by the following equation:

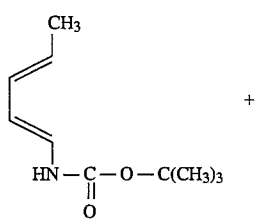

+

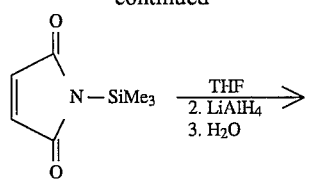

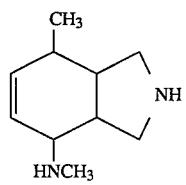

NMR spectroscopy can be used in this case to detect the cis-arrangement of all substituents of the cyclohexene ring to each other.

The reaction of (II) with (III), in which the compounds (III) can also be employed in the form of their salts, such as, for example, the hydrochlorides, is preferably carried out in a diluent, such as dimethyl sulphoxide, N,N-dimethylformamide, N-methylpyrrolidone, hexamethylphosphoric triamide, sulpholane, acetonitrile, water, an alcohol, such as methanol, ethanol, n-propanol, isopropanol, glycol monomethyl ether or pyridine. Mixtures of these diluents can also be used.

Acid-binders which can be used are all customary inorganic and organic acid-binding agents. These preferably include the alkali metal hydroxides, alkali metal carbonates, and organic amines and amidines. The following may be mentioned individually as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. In general, the process is carried out between approximately 20° and 200° C., preferably between 80° and 180° C.

The reaction can be carried out under atmospheric pressure, but also under elevated pressure. In general, the process is carried out at pressures between approximately 1 and 100 bar, preferably between 1 and 10 bar.

When carrying out the process according to the invention, 1 to 15 mol, preferably 1 to 6 mol, of the compound (III) are employed per mole of the compound (II).

Free amino groups can be protected during the reaction by a suitable amino protective group, for example by the tert.-butoxycarbonyl radical, and set free again after the reaction has ended by treatment with a suitable acid, such as hydrochloric acid or trifluoroacetic acid (see Houben-Weyl, Methoden der Organischen Chemie [Methods of Organic Chemistry], Vol. E4, p. 144 (1983); J. F. W. McOmie, Protective Groups in Organic Chemistry (1973), page 43).

The esters according to the invention are obtained by reaction of an alkali metal salt of the carboxylic acid on which they are based, which can optionally be protected on the N atom by a protective group, such as the tert.-butoxycarbonyl radical, with suitable halogenoalkyl derivatives in a solvent, such as dimethylformamide, dimethylacetamide, N-methylpyrrolidone, dimethyl sulphoxide or tetramethyl urea, at temperatures from approximately 0° to 100° C., preferably 0° to 50° C.

The acid addition salts of the compounds according to the invention are prepared in the customary manner, for example by dissolving the betaine in a sufficient amount of aqueous acid and precipitating the salt with a water-miscible organic solvent, such as methanol, ethanol, acetone or acetonitrile. It is also possible to heat equivalent amounts of betaine and acid in water or an alcohol, such as glycol monomethyl ether, and subsequently to evaporate the mixture to dryness or to remove the precipitated salt by filtration with suction. Pharmaceutically utilizable salts are to be understood as meaning, for example, the salts of hydrochloric acid: sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal salts or alkaline earth metal salts of the carboxylic acids according to the invention are obtained, for example, by dissolving betaine in a substoichiometric amount of alkali metal hydroxide solution or alkaline earth metal hydroxide solution, removing the undissolved betaine by filtration and evaporating the filtrate to dryness. Pharmaceutically acceptable salts are the sodium, potassium or calcium salts. The corresponding silver salts are obtained by reacting an alkali metal salt or alkaline earth metal salt with a suitable silver salt, such as silver nitrate.

In addition to the compounds according to the invention mentioned in the examples, it is also possible to prepare those listed in the table below, which can exist in racemic and in enantiomerically pure or diastereomerically pure form:

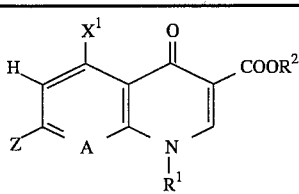

| $R^1$ | $R^2$ | $X^1$ | Z | A |
| --- | --- | --- | --- | --- |
| cyclopropyl | H | H | 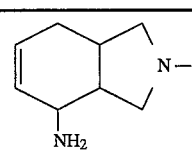 | C—H |
| cyclopropyl | ethyl | H | 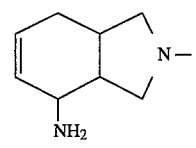 | C—H |
| cyclopropyl | H | H | 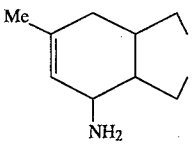 | C—Cl |
| cyclopropyl | H | H | 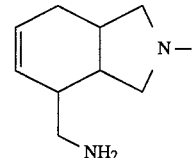 | C—Cl |
| cyclopropyl | ethyl | H | 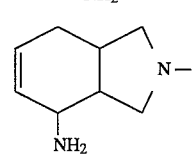 | C—Cl |
| cyclopropyl | —$CH_2$—$CH_2$—$NH_2$ | H | 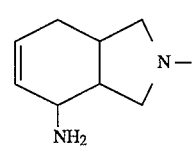 | C—Cl |
| cyclopropyl | —$CH_2$—$CH_2$—$OCH_3$ | H | 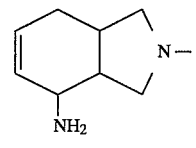 | C—Cl |

-continued

| R¹ | R² | X¹ | Z | A |
|---|---|---|---|---|
| cyclopropyl | H | H | methyl-substituted cyclohexenyl-fused pyrrolidine with NH₂ | C—F |
| cyclopropyl | H | H | cyclohexenyl-fused pyrrolidine with CH₂NH₂ | C—F |
| cyclopropyl | ethyl | H | cyclohexenyl-fused pyrrolidine with NH₂ | C—F |
| cyclopropyl | —CH₂—CH₂—NH₂ | H | cyclohexenyl-fused pyrrolidine with NH₂ | C—F |
| cyclopropyl | —CH₂—CH₂—OCH₃ | H | cyclohexenyl-fused pyrrolidine with NH₂ | C—F |
| cyclopropyl | H | F | cyclohexyl-fused pyrrolidine with NH | C—F |
| cyclopropyl | ethyl | F | cyclohexenyl-fused pyrrolidine with NH₂ | C—F |
| cyclopropyl | H | NH₂ | cyclohexenyl-fused pyrrolidine with NH₂ | C—F |
| cyclopropyl | H | —CF₃ | cyclohexenyl-fused pyrrolidine with NH₂ | C—F |

-continued

[Structure: pyridone core with X¹, H, Z, A substituents, COOR² group, and N-R¹]

| R¹ | R² | X¹ | Z | A |
|---|---|---|---|---|
| ethyl | H | H | octahydropyrrolo[3,4-b]pyridinyl (NH) | C—Cl |
| ethyl | ethyl | H | amino-tetrahydroisoindolinyl | C—Cl |
| 2,4-difluorophenyl | H | H | octahydropyrrolo[3,4-b]pyridinyl (NH) | C—Cl |
| 2,4-difluorophenyl | ethyl | H | amino-tetrahydroisoindolinyl | C—Cl |
| ethyl | H | H | octahydropyrrolo[3,4-b]pyridinyl (NH) | C—F |
| ethyl | H | H | amino-tetrahydroisoindolinyl | C—F |
| ethyl | ethyl | H | amino-tetrahydroisoindolinyl | C—F |
| 2,4-difluorophenyl | H | H | octahydropyrrolo[3,4-b]pyridinyl (NH) | C—F |
| 2,4-difluorophenyl | H | H | amino-tetrahydroisoindolinyl | C—F |

-continued

| R¹ | R² | X¹ | Z | A |
|---|---|---|---|---|
| 2,4-difluorophenyl | ethyl | H | 4-amino-cyclohexene-fused pyrrolidine (N-linked) | C—F |
| cyclopropyl | H | H | octahydroisoquinoline (NH, N-linked) | C—CH₃ |
| cyclopropyl | H | H | 4-amino-cyclohexene-fused pyrrolidine (N-linked) | C—CH₃ |
| cyclopropyl | H | H | octahydroisoquinoline (NH, N-linked) | N |
| cyclopropyl | H | H | 4-amino-cyclohexene-fused pyrrolidine (N-linked) | N |
| cyclopropyl | ethyl | H | 4-amino-cyclohexene-fused pyrrolidine (N-linked) | N |
| 2,4-difluorophenyl | H | H | octahydroisoquinoline (NH, N-linked) | N |
| 2,4-difluorophenyl | H | H | 4-amino-cyclohexene-fused pyrrolidine (N-linked) | N |
| 2,4-difluorophenyl | ethyl | H | 4-amino-cyclohexene-fused pyrrolidine (N-linked) | N |

-continued
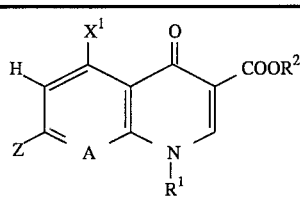
| R¹ | R² | X¹ | Z | A |
|---|---|---|---|---|
| 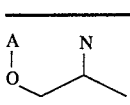 | H | H | 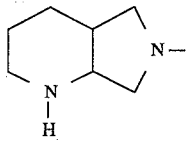 | see R¹ |
| 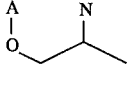 | H | H | 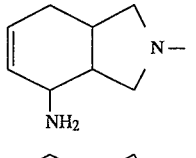 | see R¹ |
| 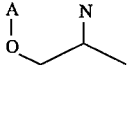 | ethyl | H | 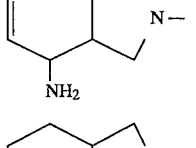 | see R¹ |
| cyclopropyl | H | Br | 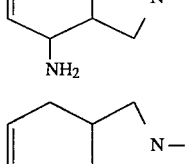 | C—F |
| cyclopropyl | H | Cl | 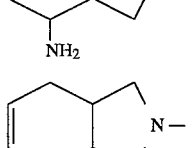 | C—F |
| cyclopropyl | ethyl | Br | 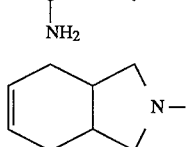 | C—Cl |
| cyclopropyl | H | Cl | 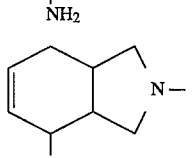 | C—Cl |
| cyclopropyl | H | H | 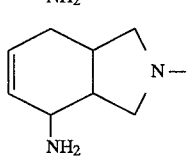 | C—CH=CH₂ |
| cyclopropyl | H | H |  | C—CCH |

| R¹ | R² | X¹ | Z | A |
|---|---|---|---|---|
| cyclopropyl | H | H | (octahydro-pyrrolo-piperidine with N-CH=CH-COOEt substituent) | C—Cl |
| cyclopropyl | H | H | (octahydro-pyrrolo-piperidine with N-CH₂-C(=O)-CH₃ substituent) | C—Cl |

The compounds according to the invention have a powerful antibiotic activity and, while having a low toxicity, display a broad antibacterial spectrum against Gram-positive and Gram-negative microorganisms, in particular against Enterobacteriaceae; in particular also against those which are resistant to a range of antibiotics, such as, for example, penicillins, cephalosporins, aminoglycosides, sulphonamides and tetracyclines.

These valuable properties allow them to be used as chemotherapeutic active compounds in medicine and as preservatives for inorganic and organic materials, in particular any type of organic material, for example polymers, lubricants, colours, fibres, leather, paper and wood, foodstuffs and water.

The compounds according to the invention are active against a very broad spectrum of microorganisms. Using these compounds, it is possible to combat Gram-negative and Gram-positive bacteria and bacteria-like microorganisms and to prevent, alleviate and/or cure the diseases caused by these pathogens.

The compounds according to the invention are distinguished by an improved activity against dormant and resistant microorganisms. In the case of dormant bacteria, i.e. bacteria which show no detectable growth, the compounds act far below concentrations of previously known substances. This applies not only to the amount to be employed but also to the speed of destruction. Such results were observed in the case of Gram-positive and -negative bacteria, in particular in *Staphylococcus aureus, Pseudomonas aeruginosa, Enterococcus faecalis* and *Escherichia coli*.

The compounds according to the invention also show surprisingly increased activity against bacteria which are classified as less sensitive to comparable substances, in particular resistant *Staphylococcus aureus, Escherichia coli, Pseudomonas aeruginosa* and *Enterococcus faecalis*.

The compounds according to the invention are particularly effective against bacteria and bacteria-like microorganisms. They are therefore particularly suitable for the prophylaxis and chemotherapy of local and systemic infections in human and veterinary medicine caused by these pathogens.

The compounds are furthermore suitable for combating protozoonoses and helminthoses.

The compounds according to the invention can be used in the form of a range of pharmaceutical preparations. Preferred pharmaceutical preparations which may be mentioned are tablets, coated tablets, capsules, pills, granules, suppositories, solutions, suspensions and emulsions, pastes, ointments, gels, cremes, lotions, powders and sprays.

The minimum inhibitory concentrations (MIC) were determined by the serial dilution test on Iso-sensitest agar (Oxoid). For each test substance, a series of agar plates was prepared which contained concentrations of the active substance which decreased at a rate of in each case twice the dilution factor. The agar plates were inoculated using a multipoint inoculator (Denley). For inoculation, overnight cultures of the pathogens were used which had previously been diluted in such a manner that each inoculation point contained approximately $10^4$ colony-forming units. The inoculated agar plates were incubated at 37° C., and the microbial growth was observed after approx. 20 hours. The MIC value (µg/ml) indicates the lowest active compound concentration at which no growth could be detected by the naked eye.

The MIC values of some of the compounds according to the invention are listed in the table below in comparison with 7-(3-aminopyrrolidin-1-yl)-1-cyclopropyl-8-fluoro-1,4-dihydro-4-oxo-3-quinolinecarboxylic acid (journal of Medicinal Chemistry 35, 198 (1992)) as reference compound.

TABLE

MIC values

| Species | Strain | Example No. 7 | 8 | 20 | 21 | Reference |
|---|---|---|---|---|---|---|
| E. coli | Neumann | 0.0078 | 0.015 | 0.03 | 0.015 | 0.031 |
|  | 455/7 | 0.5 | 0.5 | 1 | 0.5 | 1 |
| Klebsiella pneumoniae | 8085 | 0.015 | 0.03 | 0.03 | 0.3 | 0.062 |
|  | 63 | 0.015 | 0.03 | 0.03 | 0.3 | 0.062 |
| Providencia sp. | 12012 | 0.015 | 0.06 | 0.06 | 0.06 | 0.06 |
|  | 12052 | 1 | 1 | 1 | 1 | 2 |
| Mirococcus luteus | 9341 | 0.03 | 0.06 | 0.06 | 0.125 | 0.5 |
| Staphylococcus aureus | ICB 25701 | 0.06 | 0.06 | 0.25 | 0.25 | 4 |
|  | 1756 | 0.0039 | 0.0078 | 0.015 | 0.015 | 0.125 |
|  | 133 | 0.0039 | 0.0078 | 0.03 | 0.015 | 0.125 |
|  | 25768 | 2 | 2 | 4 | 2 | 16 |
| Enterococcus faecalis | 27101 | 0.015 | 0.06 | 0.06 | 0.06 | 0.25 |
|  | 9790 | 0.03 | 0.06 | 0.06 | 0.06 | 0.25 |
| Acinetobacter caloaceticus | 14068 | 0.015 | 0.03 | 0.06 | 0.03 | 0.25 |

PREPARATION OF THE INTERMEDIATES

Example A

4-Methylamino-1,3,3a,4,7,7a-hexahydroisoindole

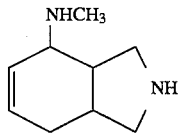

Method I 14.4 g (60 mmol) of 70% 1-(tert.-butyloxycarbonylamino)-1,3-butadiene [J. Org. Chem. 43, 2164 (1978)] in the form of a solution in 30 ml of absolute tetrahydrofuran are added dropwise to 10.1 g (60 mmol) of N-trimethylsilylmaleimide [J. Org. Chem. 40, 24 (1975)] in 30 ml of absolute tetrahydrofuran, this mixture having been introduced previously. After the exothermal reaction has subsided, refluxing is continued for 1 hour.

The cold reaction mixture is then added dropwise under nitrogen to 7.6 g (0.2 mol) of lithium aluminiumhydride in 200 ml of absolute tetrahydrofuran, this mixture having been introduced previously. This is then refluxed for 14 hours. When the reaction mixture is cold, 7.6 g of water in 23 ml of tetrahydrofuran, 7.6 g of 10% strength sodium hydroxide solution and 22.8 g of water are added dropwise in succession. The salts are filtered off, and the filtrate is concentrated in vacuo. The residue (10.3 g) is distilled at 87° C./0.8 mbar.

The distillate is taken up in 80 ml of absolute pentane, the mixture is filtered, and the product is crystallized by cooling to −70° C.

Yield: 3.3 g, melting point: 72°–82° C.

Treatment with an equimolar amount of 2N hydrochloric acid gives 4-methylamino-1,3,3a,4,7,7a-hexahydroisoindole dihydrochloride of melting point 265°–268° C. (from methanol).

Method II a) 4-(Tert.-butyloxycarbonylamino)-1,3-dioxo-1,3,3a,4,7,7a-hexahydroisoindole, 48.8 g (0.5 mol) of maleimide dissolved in 200 ml of absolute tetrahydrofuran are initially introduced, and 120 g (0.5 mol) of approximately 70% 1-(tert.-butyloxycarbonylamino)-1,3-butadiene in the form of a solution in 500 ml of absolute tetrahydrofuran are added dropwise, the temperature being maintained at 20° to 30° C. Stirring is continued overnight at room temperature. The mixture is then concentrated and recrystallized from ethyl acetate. This gives 57 g of product with a melting point of 177° to 182° C. A further 13 g with a melting point of 158° to 160°C. are obtained from the mother liquor.

b) 4-Methylamino-1,3,3a,4,7,7a-hexahydroisoindole, 27.1 g (0.71 mol) of lithium aluminium hydride are introduced into 300 ml of absolute tetrahydrofuran, under nitrogen, and a solution of 57 g (0.21 mol) of 4-(tert.-butyloxycarbonylamino)-1,3-dioxo-1,3,3a,4,7,7a-hexahydroisoindole in 570 ml of absolute tetrahydrofuran is added dropwise. The mixture is subsequently refluxed overnight. When the mixture is cold, 27.1 g of water in 82 ml of tetrahydrofuran, 27.1 g of 10% strength sodium hydroxide solution and 81.3 g of water are added dropwise in succession to the batch. The salts are filtered off with suction and washed with tetrahydrofuran, and the filtrate is concentrated in vacuo. The residue is distilled under a high vacuum.

Yield: 19.1 g

Example B

4-Amino-1,3,3a,4,7,7a-hexahydroisoindole

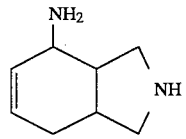

13.3 g (50 mmol) of 4-tert.-butyloxycarbonylamino-1,3-dioxo-1,3,3a,4,7,7a-hexahydroisoindole (from Example A, Method II) are stirred in 166 ml of trifluoroacetic acid overnight at room temperature. The trifluoroacetic acid is then distilled off at 10 mbar, and the residue is freed from residual acid at 50° under a high vacuum. The product is subsequently taken up in absolute tetrahydrofuran and concentrated in vacuo. The residue is taken up in 100 ml of absolute tetrahydrofuran and the mixture is added dropwise under nitrogen to a solution of 11.3 g (0.3 mol) of lithium aluminiumhydride in 300 ml of absolute tetrahydrofuran. The mixture is subsequently refluxed for 16 hours. When the mixture is cold, 11.3 g of water in 34 ml of tetrahydrofuran, 11.3 ml of 10% strength sodium hydroxide solution and 34 ml of water are added dropwise in succession. The precipitate is filtered off with suction and washed with tetrahydrofuran. The filtrate is concentrated, and the residue is distilled.

Yield: 2.2 g, content: 92% (determined by gas chromatography) Boiling point: 70°/0.2 mbar Example C 7-Methyl-4-methylamino-1,3,3a,4,7,7a-hexahydroisoindole

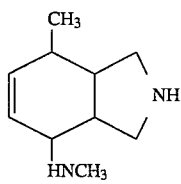

In analogy to Example A, Method I 21.9 g (0.12 mol) of 1-(tert.-butyloxycarbonylamino)-1,3-pentadiene are reacted with 20.3 g (0.12 mol) of N-trimethylsilylmaleimide and the product is subsequently reduced using 15.2 g (0.4 mol) of lithium aluminiumhydride. The crude product is recrystallized from tetrahydrofuran.

Yield: 6.2 g, melting point: 106°–108° C.

Example D

7-Isopropyl-4-methylamino-1,3,3a,4,7,7a-hexahydroisoindole

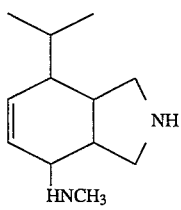

50 g (0.24 mol) of 1-(tert.-butyloxycarbonylamino)-5-methyl-1,3-hexadiene together with 23 g (0.24 mol) of maleimide are stirred under reflux for 24 hours in 75 ml of ethanol and 75 ml of water. When the mixture is cold, the solid is filtered off with suction and washed with water, and, after drying, 56.3 g (76% of theory) of a solid of melting point 192°–195° C. are obtained. 15 g (0.049 mol) together with 11 g (0.29 mol) of lithium aluminium hydride in 300 ml of tetrahydrofuran are stirred for 10 hours under reflux. After cooling, the mixture is hydrolysed using 10 ml of water. The precipitate is filtered off with suction and washed with tetrahydrofuran, and the combined filtrates are evaporated to dryness. This gives 8.7 g of a solid which is purified by crystallization (petroleum ether/ethyl acetate=1:5).

Yield: 43.5 g (51% of theory), Melting point: 76°–81° C.

Example E

4-Amino-7-isopropyl-1,3,3a,4,7,7a-hexahydroisoindole

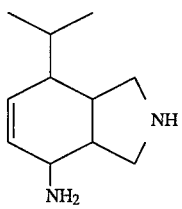

The compound is prepared analogously to Example B.
$^1$H NMR (200 MHz, CDCl$_3$): δ=0.95 (6H); 2.3–2.7 (m, 7H); 5.75 (2H). MS: m/e (% tel. int.): 180 [M$^+$] (7); 163 (45); 120 (100); 67 (100).

Example F

4-Hydroxymethyl-1,3,3a,4,7,7a-hexahydroisoindole

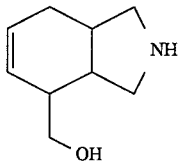

25 g (0.22 mol) of methyl 2,4-pentadienecarboxylate in 100 ml of dioxane and 20 g (0.21 mol) of maleimide are stirred under reflux for 40 hours. The oil obtained after concentration (51 g) is stirred for 16 hours under reflux in 350 ml of tetrahydrofuran and 20 g (0.52 mol) of lithium aluminiumhydride. After cooling, the mixture is hydrolysed using 63 ml of water, 63 ml of 10 percent strength sodium hydroxide solution and finally 60 ml of water, and the precipitate is filtered off with suction and washed several times using tetrahydrofuran. The combined filtrates are concentrated and distilled under a high vacuum.

Yield: 10 g (30% of theory) Boiling point: 96°–115° C./0.07 mbar.

Example G

4-Methylaminomethyl1-1,3,3a,4,7,7a-hexahydroisoindole

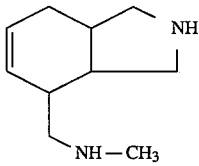

a) 1-tert.-Butyloxycarbonylamino-2,4-Pentadiene
Reaction of 1-amino-2,4-pentadiene (P. A. Grieco et al., Tetrahedron 42, 2847 [1986]) with di-tert.-butyl carbonate in dioxane at room temperature for
12 hours at pH 8–10 gives 1-tert.-butyloxycarbonylamino-2,4-pentadiene as a pale oil in quantitative yield.
$^1$H NMR (200 MHz, CDCl$_3$): δ=1.45 (9H), 3.78 (2H); 4.65 (br., 1H); 5.05–5.21 (m, 2H); 5.60–5.75 (m, 1H); 6.08–6.42 ppm (m, 2H).
4-tert.-Butyloxycarbonylaminomethyl-1,3-dioxo-1,3,3a,4,7, 7a-hexahydroisoindole, 30 g (0.16 mol) of 1-tert.-butyloxycarbonylamino-2,4-pentadiene together with 16 g (0.16 mol) of maleimide are stirred under reflux for 12 hours in 120 ml of dioxane. After the mixture has cooled, it is concentrated to half its volume, and the solid is filtered off with suction.

Yield: 35.3 g (76%) Melting point: 197.5°–198.5° C.

c) 4-Methylaminomethyl-1,3,3a,4,7,7a-hexahydroisoindole, 4-tert.-Butyloxycarbonylaminomethyl-1,3-dioxo-1,3,3a,4,7,7a-hexahydroisoindole is reduced using lithium aluminium hydride analogously to the procedure described in Example A, Method IIb: yellow oil.

Boiling point=78° C./0.05 mbar.

Example H

4-Aminomethyl-1,3,3,a,4,7,7a-hexahydroisoindole

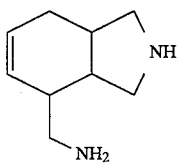

4-tert.-Butyloxycarbonylaminomethyl-1,3-dioxo-1,3,3a,4,7,7a-hexahydroisoindole is employed analogously to the procedure described in Example B.

Boiling point=135°–140° C./0.1 mbar.

Example I

6-Methyl-4-methylamino-1,3,3a,4,7,7a-hexahydroisoindole

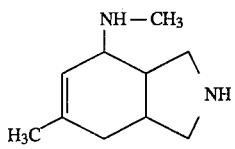

a) 4-(tert.-Butyloxycarbonylamino)-1,3-dioxo-6-methyl-1,3,3a,4,7,7a-hexahydroisonindole, The reaction is carried out using 1-tert.-butyloxycarbonylamino-3-methyl-1,3-butadiene in dioxane analogously to Example A/Method IIa.

Melting point: 135° C.

b) 6-Methyl-4-methylamino-1,3,3a,4,7,7a-hexahydroisoindole,

In analogy to Example B, 5.6 g (20 mmol) of the product of Example Ma) are refluxed for 15 hours together with 2.2 g (60 mmol) of lithium aluminium hydride in 60 ml of tetrahydrofuran. Working-up by distillation gives 1.2 g of the product of boiling point 68°–71° C./0.2–0.3 mbar.

Example J

4-Amino-7-methyl-1,3,3a,4,7,7a-hexahydroisoindole

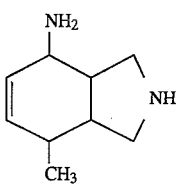

a) 4-tert.-Butyloxycarbonylamino)-1,3-dioxo-7-methyl-1,3,3a,4,7,7a-hexahydroisoindole, The reaction is carried out using 1-tert.-butyloxycarbonylamino-1,3-pentadiene analogously to Example A/Method IIa, and the reaction product is recrystallized from dioxane.

Yield: 79% Melting point: 298°–211° C.

b) 4-Amino-7-methyl-1,3,3a,4,7,7a-hexahydroisoindole,

Analogously to Example B, the product of Example Na) is employed, giving the free amine as an oil of boiling point 83°–92° C./0.1 mbar, which crystallizes upon standing. Content: 90% (according to gas chromatogram).

Example K

4-Amino-7-cyclopropyl-1,3,3a,4,7,7a-hexahydroisoindole

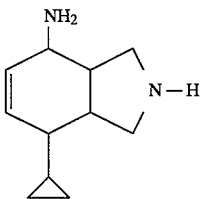

a) 4-(tert.-Butoxycarbonylamino)-7-cyclopropyl-1,3-dioxo-1,3,3a,4,7,7a-hexahydroisoindole 1-tert.-Butoxycarbonylamino-4-cyclopropyl-1,3-butadiene (prepared analogously to the method described in J. Org. Chem. 43., 2164 [1978]; IR (CCl$_4$): 330, 1720, 1605 cm$^{-1}$) is reacted analogously to Example A/Method II.

Melting point: 195.5°–196.5° C.

b) 4-Amino-7-cyclopropyl-1,3,3a,4,7,7a-hexahydroisoindole

Analogously to Example B, the product of Example Oa is reacted with lithium aluminiumhydride to give a viscous oil. FAB MS (glycerol/DMSO): m/e 179 [M+H]$^+$).

Example L

1-Cyclopropyl-7-fluoro-1,4-dihydro-4-oxo-3-quinolinecarboxylic acid

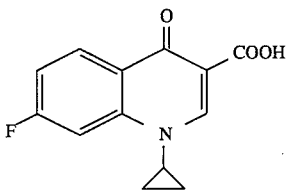

a) Diethyl (2,4-difluorobenzoyl)malonate 13.47 g (0.14 mol) of magnesium chloride are introduced at 0° C. into 140 ml of absolute acetonitrile, and 23.5 g (0.14 mol) of diethyl malonate are added dropwise, while cooling with an ice-bath. 28.17 g (0.28 mol) of triethylamine are subsequently added dropwise at 0° C, 22.4 g (0.14 mol) of 2,4-difluorobenzoyl fluoride (U.S. Pat. No. 4,847,442) are added dropwise at 0° after the mixture has been stirred for 30 minutes, and stirring is continued overnight while the mixture comes to room temperature. The mixture is treated with 90 ml of 18% strength hydrochloric acid and extracted using methylene chloride, and the methylene chloride phase is dried over sodium sulphate and concentrated in vacuo.

Crude yield: 41.4 g b) Ethyl (2,4-difluorobenzoyl)acetate 41.4 g of the crude diethyl (2,4-difluorobenzoyl)malonate in 130 ml of water and 170 mg of p-toluenesulphonic acid are refluxed for 8.5 hours. The mixture is extracted using methylene chloride, and the methylene chloride phase is washed with water, dried over sodium sulphate and concentrated in vacuo.

Crude yield: 29.0 g c) Ethyl 2-(2,4-difluorobenzoyl)-3-ethoxyacrylate 29.0 g (0,127 mol) of the product of b. are heated for two hours at 150°–160° C. in 29.98 g (0.20 mol) of ethyl orthoformate and 34.5 g (0.34 mol) of acetic anhydride. All volatile constituents are distilled off under a high vacuum at a bath temperature of up to 100° C., and the crude product is directly reacted further.

Crude yield: 28.4 g d) Ethyl 3-cyclopropylamino-2-(2,4-difluorobenzoyl)acrylate 6.27 g (0.11 tool) of cyclopropylamine are added dropwise at 0° C., in 220 tool of ethanol, to 28.4 g of the crude product of c., and stirring is continued for two hours at room temperature. 220 ml of water are added, and the product which has crystallized out is isolated.

Yield: 22.2 g (54% of theory) Melting point: 71° C.

e) Ethyl 1-cyclopropyl-7-fluoro-1,4-dihydro-4-oxo-3-quinolinecarboxylate 2.95 g (0.01 mol) of the product obtained under d. are heated for six hours at 140° C. in 33 ml of dimethylformamide and 0.63 g (0,015 mol) of sodium fluoride. After cooling, the mixture is treated with water, and the product which has crystallized out is isolated and dried at 100° C.

Yield: 2.1g (76% of theory) Melting point: 190°–192° C.

f) 1-Cyclopropyl-7-fluoro-1,4-dihydro-4-oxo-3-quinolinecarboxylic acid 2.75 g (0.01 mol) of ethyl 1-cyclopropyl-7-fluoro-1,4-dihydro-4-oxo-3-quinolinecarboxylate are refluxed for four hours in a mixture of 12 ml of acetic acid, 12 ml of water and 1.2 ml of concentrated sulphuric acid. The cooled reaction mixture is poured into ice-water, and the precipitate is filtered off, washed with water and dried at 100° C. in a drying cupboard.

Yield: 2.2 g (89% of theory) Melting point: 291° C. (decomposition)

Example M

8-Chloro-1-cyclopropyl-7-fluoro-1,4-dihydro-4-oxo-3-quinolinecarboxylic acid

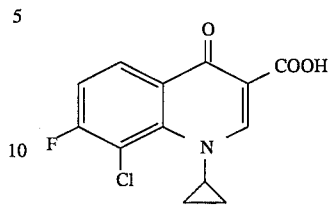

a) 3-Chloro-2,4-difluorobenzoic acid 200 g (0.92 mol) of 3-chloro-2,4-difluorobenzotrifluoride are added to 400 ml of concentrated sulphuric acid, and the mixture is heated for three hours at 118° C., with stirring. After cooling, it is poured onto 500 g of ice, and the white solid is filtered off with suction and dried in vacuo at 60° C.

Yield: 172 g (97% of theory) Melting point: 173°–175° C.

b) 3-Chloro-2,4-difluoro-benzoyl chloride

Thionyl chloride is metered at 70° C. to a suspension of 235 g (1.22 mol) of 3-chloro-2,4-difluorobenzoic acid in 800 ml of toluene and 3 ml of dimethylformamide until a clear solution has formed and evolution of gas is no longer observed. The toluene and excess thionyl chloride are then distilled off, and the product is subsequently obtained by distillation.

Yield: 256 g (99% of theory) Boiling point: 108°–110° C./22 mbar c) Diethyl (3-chloro-2,4-difluorobenzoyl)malonate 3.9 g (0.16 mol) of magnesium are introduced into 8.6 ml of ethanol, and the reaction is started up using carbon tetrachloride. A solution of 23.1 g (0.144 mol) of diethyl malonate in 16.3 ml of ethanol is added dropwise at an internal temperature of 50°–60° C. in such a manner that the temperature is maintained. The mixture is subsequently stirred for one hour at 60° C. A solution of 31.3 g (0.148 mol) of 3-chloro-2,4-difluorobenzoyl chloride in 16 ml of toluene is then added dropwise at −10° to −5° C., and stirring is continued for one hour at 0° C. and subsequently overnight while the mixture comes to room temperature. The reaction mixture is poured into ice-water, acidified using 10 ml of concentrated sulphuric acid and extracted using toluene. The toluene phase is washed using saturated sodium chloride solution, and the solvent is removed in vacuo.

Crude yield: 49.9 g d) Ethyl (3-chloro-2,4-difluorobenzoyl)acetate 49.9 g of the crude product obtained in c. are refluxed for 4.5 hours in 60 ml of water and 1.83 g of p-toluenesulphonic acid. When the batch is cold, it is extracted using methylene chloride, and the methylene chloride phase is washed using saturated sodium chloride solution, dried over sodium sulphate and concentrated in vacuo.

Crude yield: 37.3 g e) Ethyl 2-(3-chloro-2,4-difluorobenzoyl)-3-ethoxyacrylate 37.3 g of the crude product obtained in d. together with 33.4 g (0,226 mol) of ethyl orthoformate and 37.2 g (0,365 mol) of acetic anhydride are heated for two hours at 150°–160° C. Excess reagent is removed first in vacuo and subsequently under a high vacuum up to a bath temperature of 100° C.

Crude yield: 40.2 g f) Ethyl 2-(3-chloro-2,4-difluorobenzoyl)-3-cyclopropylaminoacrylate 40.2 g of the crude product obtained in e. are dissolved in 100 ml of ethanol and 9.6 g (0.168 mol) of cyclopropylamine are added dropwise, with ice-bath cooling. Stirring is continued for 30 minutes at room temperature, and the reaction mixture is subsequently treated with 100 ml of ice-water. The product which has precipitated is isolated, washed with water and dried at 100° C.

Yield: 30.8 g (63% of theory based on (c)) Melting point: 101°–104° C.

g) Ethyl 8-chloro-1-cyclopropyl-7-fluoro-1,4-dihydro-4-oxo-3-quinolinecarboxylate 15 g (0,046 mol) of the crude product obtained in f. in 90 ml of dimethylformamide and 7.2 g (0.052 mol) of potassium carbonate are heated for two hours at 140°–150° C. When the batch is cold, it is poured into water, and the product is isolated, washed with water and dried at 100° C.

Yield: 13.5 g (95% of theory) Melting point: 149° 153° C.

h) 8-Chloro-1-cyclopropyl-7-fluoro-1,4-dihydro-4-oxo-3-quinolinecarboxylic acid 13.5 g (0.044 mol) of the ester obtained in g. are refluxed for four hours in a mixture of 52 ml of acetic acid, 52 ml of water and 5.2 ml of concentrated sulphuric acid. When the batch is cold, it is poured into ice-water, and the product is isolated, washed thoroughly with water and dried at 100° C.

Yield: 11.6 g (94% of theory) Melting point: 192°–193° C.

Example N

1-Cyclopropyl-5,7,8-trifluoro-1,4-dihydro-4-oxo-3-quinolinecarboxylic acid

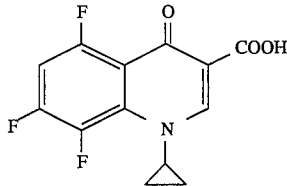

36.7 g (0.118 mol) of ethyl 1-cyclopropyl-5,7,8-trifluoro-1,4-dihydro-4-oxo-3-quinolinecarboxylate (JP 1,308,281) are introduced into a mixture of 285 ml of acetic acid, 190 ml of water and 30 ml of concentrated sulphuric acid, and the mixture is refluxed for two hours. The batch is poured onto ice, and the product is isolated, washed with water and dried at 100° C.

Yield: 31.6 g (94% of theory) Melting point: 218°–220° C.

Example O

1-Ethyl-7,8-difluoro-1,4-dihydro-4-oxo-3-quinolinecarboxylic acid

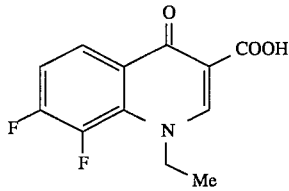

a) 2,3,4-Trifluorobenzoyl chloride 1000 g (5.68 mol) of 2,3,4-trifluorobenzoic acid are introduced in portions at 50° C. via a metering worm into 1300 ml of thionyl chloride and 5 ml of dimethylformamide. When metering in has ended, the mixture is refluxed until the evolution of gas has ceased. The excess thionyl chloride is then distilled off, and the product is distilled in vacuo.

Yield: 1027 g (93% of theory) Boiling point: 65° C./10 mbar b) Diethyl (2,3,4-trifluorobenzoyl)malonate 3.6 g (0.148 mol) of magnesium filings are introduced into 8.1 ml of ethanol, the reaction is started up using a few drops of carbon tetrachloride, and a solution of 21.8 g (0.136 mol) of diethyl malonate in 15 ml of ethanol and 58 ml of toluene is subsequently added dropwise in such a manner that the internal temperature is between 50 and 60° C. Stirring is subsequently continued for one hour at 60° C. A solution of 27.6 g (0.15 mol) of 2,3,4-trifluorobenzoyl chloride in 15.4 ml of toluene is added dropwise at −10° to −5° C., and stirring is continued for one hour at 0° C. and subsequently overnight, allowing the mixture to come to room temperature. The batch is poured into 60 ml of ice-water, treated with 9.7 ml of concentrated sulphuric acid and extracted using toluene. The toluene phase is washed with saturated sodium chloride solution and the solvent is removed in vacuo.

Crude yield: 45.2 g c) Ethyl (2,3,4-trifluorobenzoyl)acetate 45.2 g of the crude product obtained in b. are refluxed for 4.5 hours in 57 ml of water and 1.66 g of p-toluenesulphonic acid. When the batch is cold, it is extracted using methylene chloride, and the methylene chloride phase is washed using saturated sodiumchloride solution, dried over sodium sulphate and concentrated in vacuo.

Crude yield: 33 g d) Ethyl 3-ethoxy-2-(2,3,4-trifluorobenzoyl)acrylate 33 g of the product obtained in c. together with 31.5 g (0.213 mol) of ethyl orthoformate and 31.5 g (0.344 mol) of acetic anhydride are heated for two hours at 150°–160° C. Excess reagent is removed first in vacuo and then under a high vacuum up to a bath temperature of 100° C.

Crude yield: 34.5 g e) Ethyl 3-ethylamine-2-(2,3,4-trifluorobenzoyl)acrylate 9.06 g (0.03 mol) of the product obtained in d. are introduced into 60 ml of ethanol at 0° C., and 2.12 ml (0.033 mol) of a 70% strength ethylamine solution are added dropwise. Stirring is continued for four hours at room temperature, 60 ml of water are added dropwise, and the product which precipitates is isolated. It is washed with water and dried at approximately 100° C.

Yield: 5.0 g (55% of theory) Melting point: 106°–108° C.

f) Ethyl 1-ethyl-7,8-difluoro-1,4-dihydro-4-oxo-3-quinolinecarboxylate 5.0 g (0,017 mol) of the product obtained in e. together with 2.6 g (0.019 mol) of potassium carbonate in 30 ml of dimethylformamide are heated for four hours at 100° C. When the batch is cold, it is poured into ice-water, and the product is isolated, washed with water and dried at 100° C.

Yield: 3.6 g (77% of theory) Melting point: 164°–166° C.

g) 1-ethyl-7,8-difluoro-1,4-dihydro-4-oxo-3-quinolinecarboxylic acid 3.5 g of the product obtained in 2. are heated for four hours at 140° C. in a mixture of 16 ml of acetic acid, 16 ml of water and 1.6 ml of concentrated sulphuric acid. When the batch is cold, it is poured into ice-water, and the product which has precipitated is isolated, washed with water and dried at 100° C.

Yield: 3.0 g (99% of theory) Melting point: 237°–239° C.

Example P 7,8-Difluoro-1-(2,4-difluorophenyl)-1,4-dihydro-4-oxo-3-quinolinecarboxylic acid

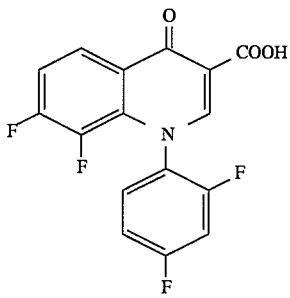

a) Ethyl 2-(2,3,4-trifluorobenzoyl)-3-(2,4-difluorophenylamino)-acrylate 9.06 g of the product obtained in Od. are reacted with 4.26 g (0.33 mol) of 2,4-difluoroaniline in analogy to Example Oe.

Yield: 7.3 g (63% of theory) Melting point: 123°–125° C.

b) Ethyl 7,8-difluoro-1-(2,4-difluorophenyl)-1,4-dihydro-4-oxo-3-quinolinecarboxylate 7.3 g (0,019 mol) of the product obtained in a. are reacted with 2.96 g (0.021 mol) of potassium carbonate analogously to Example Of.

Yield: 5.8 g (83% of theory) Melting point: 159°–160° C.

c) 7,8-Difluoro-1-(2,4-difluorophenyl)-1,4-dihydro-4-oxo-3-quinolinecarboxylic acid 5.7 g (0.016 mol) of the product obtained in b. are reacted analogously to Example Og.

Yield: 4.9 g (94% of theory) Melting point: 222°–224° C.

Example Q

8-Chloro-1-ethyl-7-fluoro-1,4-dihydro-4-oxo-3-quinolinecarboxylic acid

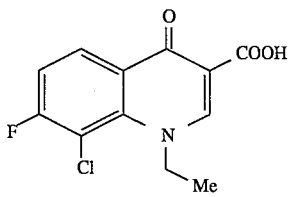

a) Ethyl 2-(3-chloro-2,4-difluorobenzoyl)-3-ethylaminoacrylate 9.55 g (0.03 mol) of ethyl 2-(3-chloro-2,4-difluorobenzoyl)-3-ethoxyacrylate are dissolved in 66 ml of ethanol. 2.12 ml (0,033 mol) of a 70% strength ethylamine solution are added dropwise with ice-cooling, and stirring is continued overnight while the mixture comes to room temperature. After an addition of water, the product is isolated, washed with water and dried.

Yield: 6.3 g ( 66% of theory) Melting point: 107°–109° C.

b) Ethyl 8-chloro-1-ethyl-7-fluoro-1,4-dihydro-4-oxo-3-quinolinecarboxylate 3. 175 g (0.01 mol) of the product obtained in a. together with 1.56 g (0. 011 mol) of potassium carbonate in 20 ml of dimethylformamide are heated for four hours at 100° C. When the batch is cold, it is poured into ice-water, and the product is isolated, washed with water and dried at 100° C.

Yield: 2.8 g (94% of theory) Melting point: 167°–169° C.

c) 8-Chloro-1-ethyl-7-fluoro-1,4-dihydro-4-oxo-3-quinolinecarboxylic acid 2.7 g (9.1 mol) of the product obtained in b. are refluxed for four hours in a mixture of 11 ml of acetic acid, 11 ml of water and 1.1 ml of concentrated sulphuric acid. The batch is treated with water, and the product is isolated, washed with water and dried at 100° C.

Yield: 2.4 g (98% of theory) Melting point: 211°–212° C.

Example R

8-Chloro-7-fluoro-1-(2,4-difluorophenyl)-1,4-dihydrobenzoyl)-4-oxo-3-quinolinecarboxylic acid

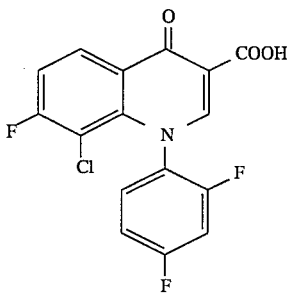

a) Ethyl 2-(3-chloro-1,4-difluorobenzoyl)-3-(2,4-difluorophenylamino)-acrylate 9.55 g (0.03 mol) of ethyl 2-(3-chloro-2,4-difluorobenzoyl)- 3-ethoxyacrylate and 4.26 g (0.033 mol) of 2,4-difluorophenylamine are reacted analogously to Example Oa.

Yield: 9.4 g (78% of theory) Melting point: 115°–116° C.

b) Ethyl 8-chloro-7-fluoro-1-(2,4-difluorophenyl)-1,4-dihydro-4-oxo-3-quinolinecarboxylate 4.01 g (0.01 mol) of the product obtained in a) are reacted with 1.56 g (0.011 mol) of potassium carbonate in dimethylformamide analogously to Example Ob.

Yield: 3.3 g (86% of theory) Melting point: 183°–185° C.

c) 8-Chloro-7-fluoro-1-(2,4-difluorophenyl)-1,4-dihydro-4-oxo-3-quinolinecarboxylic acid 3.2 g (8.4 mmol) of the ester obtained in b. are hydrolysed analogously to Example Oc.

Yield: 2.7 g (91% of theory) Melting point: 204°–206° C.

Example S

1-Cyclopropyl-7-fluoro-1,4-dihydro-8-methyl-4-oxo-3-quinolinecarboxylic acid

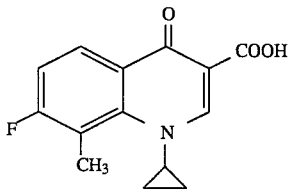

a) Ethyl 3-cyclopropylamino-2-(2,4-difluoro-3-methylbenzoyl)-acrylate 2.3 g (0. 034 mol) of cyclopropylamine are added dropwise to the solution of 10 g (0,034 mol) of ethyl 3-ethoxy-2-(2, 4-difluoro-3-methylbenzoyl)acrylate (DE 3,615,767) which is stirred at 0° C., and stirring is continued for 30 minutes at room temperature. The batch is poured into ice-water, and the product which has precipitated is washed using ethanol/water.

Yield: 6.5 g (62% of theory) Melting point: 96°–97° C.
b) Ethyl 1-cyclopropyl-7-fluoro-1,4-dihydro-8-methyl-4-oxo-3-quinolinecarboxylate 6.5 g (0.021 mol) of the product obtained in a. together with 3.4 g (0.025 mol) of potassium carbonate in 30 ml of dimethylformamide are heated to 140° C. When the batch is cold, it is poured into ice-water, and the product is isolated, washed with water and dried at 100° C.
Yield: 5.5 g (90% of theory) Melting point: 167°–168° C.
c) 1-Cyclopropyl-7-fluoro-1,4-dihydro-8-methyl-4-oxo-3-quinolinecarboxylic acid 4.5 g (0.016 mol) of the ester obtained in b, are refluxed for two hours in a mixture of 18 ml of acetic acid, 14 ml of water and 1.6 ml of concentrated sulphuric acid. The batch is poured into water, and the product is isolated and washed thoroughly with water.
Yield: 3.9 g (93% of theory) Melting point: 236°–238° C.

Example T

Ethyl 7-chloro-1-cyclopropyl-1,4-dihydro-4-oxo-1,8-naphthyridine-3-carboxylate

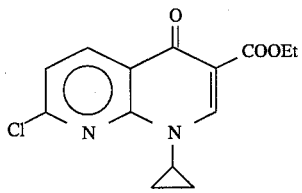

a) Diethyl (2,6-dichloronicotinoyl)malonate 7.21 g (0.075 mol) of magnesium chloride are introduced at 0° C. into 75 ml of absolute acetonitrile, and 12.12 g (0.075 mol) of diethyl malonate are added dropwise while cooling in an ice-bath. 15.34 g (0.150 mol) of triethylamine are subsequently added dropwise at 0° C., 17.0 g (0.075 mol) of 2,6-dichloronicotinoyl chloride (Helvetia Chimica Acta 59, 222, (1976)) are added dropwise at 0° C. after the mixture has been stirred for 60 minutes, and stirring is continued overnight while the mixture comes to room temperature. The mixture is treated with 80 ml of 18% strength hydrochloric acid and extracted using methyl tert.-butyl ether, and the ether phase is dried over sodium sulphate and concentrated in vacuo.
b) Ethyl (2,6-dichloronicotinoyl)acetate The crude diethyl (2,6-dichloronicotinoyl)-malonate is refluxed for 2 hours in 45 ml of water and 90 mg of p-toluenesulphonic acid. The mixture is extracted using methylene chloride, and the methylene chloride phase is washed with water, dried over sodium sulphate and concentrated in vacuo. The crude product is purified on silica gel (eluent dichloromethane).
Yield: 14.2 g (72% of theory, in two steps)
c) Ethyl 2-(2,6-dichloronicotinoyl)-3-ethoxyacrylate 43 g (0.162 mol) of the product of b. are heated for two hours at 150°–160° C. in 38.1 g (0.26 mol) of ethyl orthoformate and 42.4 g (0.42 mol) of acetic anhydride. All volatile components are distilled off under a high vacuum at a bath temperature of up to 100° C., and the crude product is directly reacted further.
Crude yield: 50.5 g
d) Ethyl 3-cyclopropylamino-2-(2,6-dichloronicotinoyl)acrylate 1.88 g (0.33 mol) of cyclopropylamine are added dropwise to 9.54 g of the crude product of c. in 66 ml of ethanol at 0° C., and stirring is continued overnight at room temperature. Water is added, and the product which has crystallized out is isolated.
Yield: 9.3 g (94% of theory) Melting point: 123°–124° C.
e) Ethyl 1-cyclopropyl-7-chloro-1,4-dihydro-4-oxo-1,8-naphthyridine-3-carboxylate 3.29 g (0.01 mol) of the product obtained in d. are heated for one hour at 100° C. in 20 ml of dimethylformamide and 1.6 g (0.019 mol) of potassium carbonate. When the batch is cold, water is added, and the product which has crystallized out is isolated and dried at 100° C.
Yield: 2.8 g (95% of theory) Melting point: 187°–190° C.

Example U

Ethyl 7-chloro-1-(2,4-difluorophenyl)-1,4-dihydro-4-oxo-1,8-naphthyridine-3-carboxylate

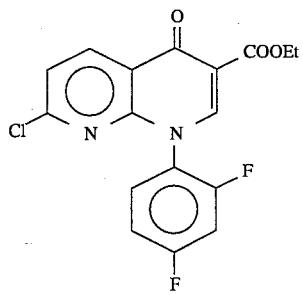

a) Ethyl 2-(2,6-dichloronicotinoyl)-3-(2,4-difluorophenylamino)-acrylate 4.26 g (0.33 mol) of 2,4-difluorophenylamine are added dropwise at 0° C., in 66 ml of ethanol, to 9.54 g of the crude product of Tc., and stirring is continued overnight at room temperature. Water is added, and the product which has crystallized out is isolated.
Yield: 8.8 g (73% of theory) Melting point: 128°–129° C.
b) Ethyl 7-chloro-1-(2,4-difluorophenyl)-1,4-dihydro-4-oxo-1,8-naphthyridine-3-carboxylate 4.01 g (0.01 mol) of the product obtained in a. are heated at 100° C. for one hour in 20 ml of dimethylformamide and 1.6 g (0,019 mol) of potassium carbonate. After the mixture has cooled, water is added, and the product which has crystallized out is isolated and dried at 100° C.
Yield: 3.5 g (96% of theory) Melting point: 200°–202° C.

Example V

8-Chloro-7-fluoro-1-(cis-2-fluorocyclopropyl)-1,4-dihydro-4-oxo-3-quinolinecarboxylic acid

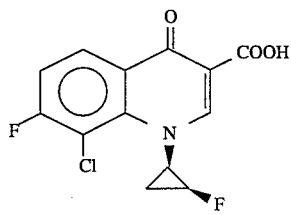

a) Ethyl 2-(3-chloro-2,4-difluorobenzoyl)-3-(cis-2-fluorocyclopropylamino)-acrylate 4.8 g (0,015 mol) of ethyl 2-(3-chloro-2,4-difluorobenzoyl)- 3-ethoxyacrylate and 1.67 g (0,015 mol) of cis-2-fluorocyclopropylamine hydrochloride (JP 3,291,258 A2)

are introduced at 0° C. into a mixture of 22.5 ml of dichloromethane and 9 ml of water. The solution of 1,275 g of sodium hydrogen carbonate in 15 ml of water is subsequently added dropwise at 0° C., and stirring is continued overnight while the mixture comes to room temperature. The phases are separated and re-extracted using dichloromethane, the dichloromethane phase is dried over sodium sulphate, and the solvent is removed in vacuo.

Yield: 4.9 g (94% of theory), oil b) Ethyl 8-chloro-7-fluoro-1-(cis-2-fluorocyclopropyl)-1,4-dihydro-4-oxo-3-quinolinecarboxylate 4.0 g (0,012 mol) of the product obtained in a. together with 1.9 g (0,014 mol) of potassium carbonate in 25 ml of dimethylformamide are heated for four hours at 100° C. When the batch is cold, it is poured into ice-water and extracted using dichloromethane. The organic phases are dried over sodium sulphate, the solvent is removed in vacuo, the crude product is stirred with acetonitrile, and the product is isolated.

Yield: 1.9 g (48% of theory) Melting point: 179°–180° C.

c) 8-Chloro-7-fluoro-1-(cis-2-fluorocyclopropyl)-1,4-dihydro-4-oxo-3-quinolinecarboxylic acid 1.0 g (3 mmol) of the product obtained in b. are refluxed for four hours in a mixture of 4 ml of acetic acid, 4 ml of water and 0.4 ml of concentrated sulphuric acid. The batch is treated with ice-water, and the product is isolated, washed with water and dried at 100° C.

Yield: 0.76 g (85% of theory) Melting point: 178°–180° C.

Example W

-Chloro-7-fluoro-1-(trans-2-fluorocyclopropyl)-1,4-dihydro-4-oxo-3-quinolinecarboxylic acid

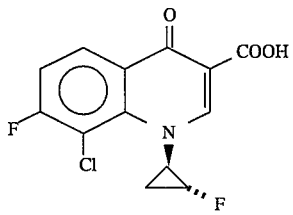

Ethyl 2-(3-chloro-2,4-difluorobenzoyl)-3-(trans-2-fluorocyclopropylamino)-acrylate 4.8 g (0,015 mol) of ethyl 2-(3-chloro-2,4-difluorobenzoyl)-3-ethoxyacrylate and 1.67 g (0,015 mol) of trans-2-fluorocyclopropylamine hydrochloride (JP 3,291,258 A2) are introduced at 0° C. into a mixture of 22.5 ml of dichloromethane and 9 ml of water. A solution of 1.275 g of sodium hydrogen carbonate in 15 ml of water is subsequently added dropwise at 0° C., and stirring is continued overnight while the mixture comes to room temperature. The phases are separated and re-extracted using dichloromethane, the dichloromethane phase is dried over sodium sulphate, and the solvent is removed in vacuo.

Yield: 5.0 g (96% of theory), oil b) Ethyl 8-chloro-7-fluoro-1-(trans-2-fluorocyclopropyl)-1,4-dihydro-4-oxo-3-quinolinecarboxylate 4.2 g (0,012 mol) of the product obtained in a. together with 1.9 g (0.014 mol) of potassium carbonate in 25 ml of dimethylformamide are heated for four hours at 100° C. When the batch is cold, it is poured into ice-water, and the product is isolated.

Yield: 3.0 g (76% of theory) Melting point: 184°–186° C.

c) 8-Chloro-7-fluoro-1-(trans-2-fluorocyclopropyl)-1,4-dihydro-4-oxo-3-quinolinecarboxylic acid 2.3 g (7 mmol) of the product obtained in b. are refluxed for four hours in a mixture of 9.2 ml of acetic acid, 9.2 ml of water and 0.9 ml of concentrated sulphuric acid. The batch is treated with ice-water, and the product is isolated, washed with water and dried at 100° C.

Yield: 1.8 g (86% of theory) Melting point: 234°–236° C.

Example X 7,8-Difluoro-1-(cis-2-fluorocyclopropyl)-1,4-dihydro-4-oxo-3-quinolinecarboxylic acid

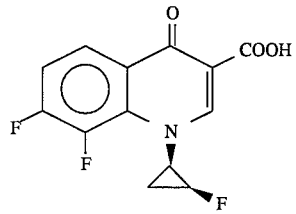

a) Ethyl 2-(2,3,4-trifluorobenzoyl)-3-(cis-2-fluorocyclopropylamino)acrylate 4.53 g (0.015 mol) of ethyl 2-(2,3,4-trifluorobenzoyl)-3-ethoxy-acrylate and 1.67 g (0.015 mol) of cis-2-fluorocyclopropylamine hydrochloride (JP 3,291,258 A2) are introduced at 0° C. into a mixture of 22.5 ml of dichloromethane and 9 ml of water. A solution of 1,275 g of sodium hydrogen carbonate in 15 ml of water is subsequently added dropwise at 0° C., and stirring is continued overnight while the mixture comes to room temperature. The phases are separated and re-extracted using dichloromethane, the dichloromethane phase is dried over sodium sulphate, and the solvent is removed in vacuo.

Yield: 4.7 g (94% of theory) Melting point: 78°–80° C.

b) Ethyl 7,8-difluoro-1-(cis-2-fluorocyclopropyl)-1,4-dihydro-4-oxo-3-quinolinecarboxylate 4.5 g (0.0136 mol) of the product obtained in a. together with 2.12 g (0.015 mol) of potassium carbonate in 25 ml of dimethylformamide are heated for two hours at 100° C. When the batch is cold, it is poured into ice-water, and the product is isolated.

Yield: 3.1 g (74% of theory) Melting point: 189°–190° C.

c) 7,8-Difluoro-1-(cis-2-fluorocyclopropyl)-1,4-dihydro-4-oxo-3-quinolinecarboxylic acid 3.1 g (10 mmol) of the product obtained in b. are refluxed for two hours in a mixture of 13 ml of acetic acid, 13 ml of water and 1.3 ml of concentrated sulphuric acid. The batch is treated with ice-water, and the product is isolated, washed with water and dried at 100° C.

Yield: 2.4 g (85% of theory) Melting point: 229°–230° C.

Example Y

1-Cyclopropyl-7-fluoro-8-trifluoromethyl-1,4-dihydro-4-oxo-3-quinolinecarboxylic acid

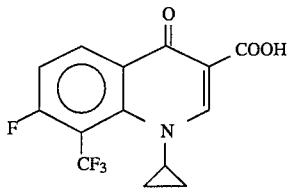

a) 2,4-Difluoro-3-trifluoromethylbenzoic acid 91 g (0.5 mol) of 1,3-difluoro-2-trifluoromethylbenzene are dissolvedunder nitrogen in a mixture of 300 ml of absolute tetrahydrofuran and 300 ml of absolute diethyl ether, and 220 ml (0.55 mol) of a 2.5M n-butyllithium solution in hexane are added dropwise at −70° C. After stirring has been continued for one hour, approximately 200 g of carbon dioxide are passed through the solution at −20° C. The mixture is subsequently allowed to defrost to 5° C., stirring is continued for one hour, and the mixture is hydrolysed using 200 ml of 2N hydrochloric acid. The aqueous phase is separated off and extracted twice using diethyl ether. The combined organic phases are washed with dilute hydrochloric acid and water, dried over magnesium sulphate and evaporated on a rotary evaporator.

Yield: 48.6 g (43% of theory) Melting point: 70°–71° C.

b) 2,4 -Difluoro-3- trifluoromethylbenzoyl chloride 19.3 g (0.085 mol) of 2,4-difluoro-3-trifluoromethylbenzoic acid are added in portions at room temperature to 130 ml of thionyl chloride. After metering has ended, the mixture is heated at 50° C. until the evolution of gas has ceased. The excess thionyl chloride is then removed by distillation and the crude product is reacted further directly.

Yield: 20.0 g (90% of theory)

c) Diethyl (2,4-difluoro-3-trifluoromethylbenzoyl)malonate 2.15 g (0.09 mol) of magnesium filings are introduced into 4.8 ml of ethanol, the reaction is started up using a few drops of carbon tetrachloride, and a solution of 12.8 g (0.075 mol) of diethyl malonate in 9 ml of ethanol and 35 ml of toluene is subsequently added dropwise in such a manner that the internal temperature is between 50 and 60° C. Stirring is then continued for one hour at 60° C. A solution of 20.0 g (0.082 mol) of 2,4-difluoro-3-trifluoromethylbenzoyl chloride in 9 ml of toluene is added dropwise at −10° to −5° C., and stirring is continued for one hour at 0° C. and subsequently while the mixture comes to room temperature. The batch is poured into 35 ml of ice-water, treated with 5.7 ml of concentrated sulphuric acid, and the mixture is extracted using toluene. The toluene phase is washed using saturated sodium chloride solution, and the solvent is removed in vacuo.

Crude yield: 30.0 g d) Ethyl (2,4-difluoro-3-trifluoromethylbenzoyl)acetate 30.0 g of the crude product obtained in c. are refluxed for 4.5 hours in 30 ml of water and 0.96 g of p-toldenesulphonic acid. When the batch is cold, it is extracted using methylene chloride, and the methylene chloride phase is washed using saturated sodiumchloride solution, dried over sodium sulphate and concentrated in vacuo.

Crude yield: 22 g e) Ethyl 3-ethoxy-2-(2,4-difluoro-3-trifluoromethylbenzoyl)-acrylate 22 g of the product obtained in d. are heated for two hours at 150°–160° C. together with 17.4 g (0.12 mol) of ethyl orthoformate and 19.4 g (0.19 mol) of acetic anhydride. Excess reagent is removed first in vacuo and then under a high vacuum up to a bath temperature of 100° C.

Crude yield: 23.1 g f) Ethyl 3 -cyclopropylamino-2-(2,4-difluoro-4-trifluoromethylbenzoyl)-acrylate 23.0 g (0.065 mol) of the product obtained in e. are introduced at 0° C. into 140 ml of ethanol, and 4.08 g (0.072 mol) of cyclopropylamine are added dropwise. Stirring is continued overnight at room temperature, 140 ml of water are added dropwise, and the product which precipitates is isolated. The product is washed with water and dried at approximately 100° C.

Yield: 9.4 g (39% of theory) Melting point: 104°–105° C.

g) Ethyl 1-cyclopropyl-7-fluoro-8-trifluoromethyl-1,4-dihydro-4-oxo-3-quinolinecarboxylate 9.0 g (0. 025 mol) of the product obtained in f. together with 3.9 g (0. 028 mol) of potassium carbonate in 50 ml of dimethylformamide are heated for four hours at 100° C. When the batch is cold, it is poured into ice-water, and the product is isolated, washed with water and dried at 100° C.

Yield: 8.1 g (98% of theory) Melting point: 154°–155° C.

h) 1-Cyclopropyl-7-fluoro-8-trifluoromethyl-1,4-dihydro-4-oxo-3-quinolinecarboxylic acid 8.0 g (0.023 mol) of the product obtained in g. are heated for two hours at 140° C. in a mixture of 30 ml of acetic acid, 30 ml of water and 3 ml of concentrated sulphuric acid. When the batch is cold, it is poured into ice-water, and the product which has precipitated is isolated, washed with water and dried at 100° C.

Yield: 7.0 g (96% of theory) Melting point: 209°–210° C.

Example Z

-Cyclopropyl-5,7-difluoro-8-trifluoromethyl-1,4-dihydro-4-oxo-3-quinolinecarboxylic acid a) 2,4,6-Trifluoro-3-trifluoromethylbenzoic acid The title compound is obtained when 1,3,5-trifluoro-2-trifluoromethylbenzene is reacted analogously to Example Ya.

Melting point: 70°–71° C.

b) 2,4,6-Trifluoro-3-trifluoromethylbenzoyl chloride 5.8 g (0,024 mol) of 2,4,6-trifluoro-3-trifluoromethylbenzoic acid are added in portions at room temperature to 40 ml of thionyl chloride. After metering has ended, the mixture is heated at 50° C. until the evolution of gas has ceased. The excess thionyl chloride is then removed by distillation, and the crude product is reacted further directly.

Yield: 6.0 g (95% of theory)

c) Diethyl (2,4,6-trifluoro-3-trifluoromethylbenzoyl)malonate 0.58 g (0.024 mol) of magnesium filings are introduced into 1.3 ml of ethanol, the reaction is started up using a few drops of carbon tetrachloride, and a solution of 3.4 g (0,019 mol) of diethyl malonate in 2.4 ml of ethanol and 9 ml of toluene is subsequently added dropwise in such a manner that the internal temperature is between 50° and 60° C. Stirring is then continued for one hour at 60° C. A solution of 5.8 g (0,027 mol) of 2,4,6-trifluoro-3-trifluoromethylbenzoylchloride in 2.5 ml of toluene is added dropwise at −10 to −5° C., and stirring is continued for one hour at 0° C. and subsequently while the mixture comes to room temperature. The batch is poured into 10 ml of ice-water, treated with 1.5 ml of concentrated sulphuric acid, and the mixture is extracted using toluene. The toluene phase is washed using saturated sodium chloride solution, and the solvent is removed in vacuo.

Crude yield: 8.6 g d) Ethyl (2,4,6-trifluoro-3-trifluoromethylbenzoyl)-acetate 8.6 g of the crude product obtained in c. are refluxed for 4.5 hours in 9 ml of water and 0.26 g of p-toluenesulphonic acid. When the batch is cold, it is extracted using methylene chloride, and the methylene chloride phase is washed using saturated sodiumchloride solution, dried over sodium sulphate and concentrated in vacuo.

Crude yield: 5.6 g e) Ethyl 3-ethoxy-2-(2,4,6-trifluoro-3-trifluoromethylbenzoyl)-acrylate 5.4 g (0.017 mol) of the product obtained in d. are heated for two hours at 150°–160° C. together with 4.0 g (0,027 mol) of ethyl orthoformate and 4.45 g (0.043 mol) of acetic anhydride. Excess reagent is removed first in vacuo and then under a high vacuum up to a bath temperature of 100° C.

Crude yield: 3.8 g f) Ethyl 3-cyclopropylamino-2-(2,4,6-trifluoro-4-trifluoromethylbenzoyl)-acrylate 3.8 g (0.01 mol) of the product obtained into e. are introduced at 0° C. in 22 ml of ethanol, and 0.63 g (0.011 mol) of cyclopropylamine are added dropwise. Stirring is continued overnight at room temperature, 22 ml of water are added dropwise, and the product which precipitates is isolated. The product is washed with water and dried at approximately 100° C.

Yield: 3.3 g (86% of theory) Melting point: 146°–148° C.

g) Ethyl 1-cyclopropyl-5,7-difluoro-8-trifluoromethyl-1,4-dihydro-4-oxo-3-quinolinecarboxylate 3.5 g (9.2 mmol) of the product obtained 3n f. together with 1.45 g (0.01 mol) of potassium carbonate in 18 ml of dimethylformamide are heated for one hour at 100° C. When the batch is cold, it is poured into ice-water, and the product is isolated and washed with water. The product is purified on silica gel, eluent cyclohexane/tetrahydrofuran 7/3.

Yield: 1.4 g (42% of theory) Melting point: 197°–198° C.

h) 1-Cyclopropyl-5,7-difluoro-8-trifluoromethyl-1,4 -dihydro-4-oxo-3-quinolinecarboxylic acid 1.4 g (3.9 mmol) of the product obtained in q. are heated for two hours at 140° C. in a mixture of 5 ml of acetic acid, 5 ml of water and 0.5 ml of concentrated sulphuric acid. When the batch is cold, it is poured into ice-water, and the product which has precipitated is isolated, washed with water and dried at 100° C.

Yield: 1.1 g (84% of theory) Melting point: 208°–210° C.

Example AA

1-Cyclopropyl-7,8-difluoro-5-trifluoromethyl-1,4-dihydro-4-oxo-3-quinolinecarboxylic acid

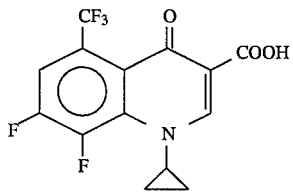

a) 2,3,4-Trifluoro-6-trifluoromethylbenzoic acid

The title compound is obtained when 1,2,3-trifluoro-5-trifluoromethylbenzene is reacted analogously to Example Ya.

Melting point: 83°–84° C.

b) 2,3,4-Trifluoro-6-trifluoromethylbenzoyl chloride 5.8 g (0,024 mol) of 2,3,4-trifluoro-6-trifluoromethylbenzoic acid are added in portions at room temperature to 40 ml of thionyl chloride. After metering has ended, the mixture is heated at 50° C. until the evolution of gas has ceased. The excess thionyl chloride is then removed by distillation and the crude product is reacted further directly.

Yield: 5.0 g (79% of theory)

c) Diethyl (2,3,4-trifluoro-6-trifluoromethylbenzoyl)malonate 0.47 g (0.019 mol) of magnesium filings are introduced into 1.0 ml of ethanol, the reaction is started up using a few drops of carbon tetrachloride, and a solution of 2.8 g (0.016 mol) of diethyl malonate in 2.0 ml of ethanol and 7.5 ml of toluene is subsequently added dropwise in such a manner that the internal temperature is between 50 and 60° C. Stirring is then continued for one hour at 60° C. A solution of 4.8 g (0.027 mol) of 2,3,4-trifluoro-6-trifluoromethylbenzoyl chloride in 2.0 ml of toluene is added dropwise at –10° to –5° C., and stirring is continued for one hour at 0° C. and subsequently while the mixture comes to room temperature. The batch is poured into 10 ml of ice-water, treated with 1.25 ml of concentrated sulphuric acid, and the mixture is extracted using toluene. The toluene phase is washed using saturated sodium chloride solution, and the solvent is removed in vacuo.

Crude yield: 6.6 g d) Ethyl (2,3,4-trifluoro-6-trifluoromethylbenzoyl)acetate 6.6 g of the crude product obtained in c. are refluxed for 4.5 hours in 7.5 ml of water and 0.21 g of p-toluenesulphonic acid. When the batch is cold, it is extracted using methylene chloride, and the methylene chloride phase is washed using saturated sodium chloride solution, dried over sodium sulphate and concentrated in vacuo.

Crude yield: 4.2 g e) Ethyl 3-ethoxy-2-(2,3,4-trifluoro-6-trifluoromethylbenzoyl)-acrylate 4.0 g (0,013 mol) of the product obtained in d. are heated for two hours at 150°–160° C. together with 3.5 g (0.024 mol) of ethyl orthoformate and 3.4 g (0.033 mol) of acetic anhydride Excess reagent is removed first in vacuo and then under a high vacuum up to a bath temperature of 100° C.

Crude yield: 2.7 g f) Ethyl 3-cyclopropylamino-2-(2,3,4-trifluoro-6-trifluoromethylbenzoyl)-acrylate 2.7 g (7.3 mmol) of the product obtained in e. are introduced at 0° C. into 16 ml of ethanol, and 0.46 g (8 mmol) of cyclopropylamine are added dropwise. Stirring is continued overnight at room temperature, 16 ml of water are added dropwise, and the product which precipitates is isolated. The product is washed with water and dried at approximately 100° C.

Yield: 2.1 g (75% of theory) Melting point: 165°–168° C.

g) Ethyl 1-cyclopropyl-7,8-difluoro-5-trifluoromethyl-1,4-dihydro-4-oxo-3-quinolinecarboxylate 2.1 g (5.5 mmol) of the product obtained in f. together with 0.88 g (6.4 retool) of potassium carbonate in 11 ml of dimethylformamide are heated for one hour at 100° C. When the batch is cold, it is poured into ice-water, and the product is isolated and washed with water.

Yield: 1.7 g ( 85% of theory) Melting point: 188°–190° C.

h) 1-Cyclopropyl-7,8-difluoro-5-trifluoromethyl-1,4-dihydro-4-oxo-3-quinolinecarboxylic acid 1.5 g (4.2 mmol) of the product obtained in g. are heated for two hours at 140° C. in a mixture of 5.5 ml of acetic acid, 5.5 ml of water and 0.55 ml of concentrated sulphuric acid. When the batch is cold, it is poured into ice-water, and the product which has precipitated is isolated, washed with water and dried at 100° C.

Yield: 1.3 g (92% of theory) Melting point: 226°–228° C.

PREPARATION OF THE ACTIVE COMPOUNDS

EXAMPLE 1

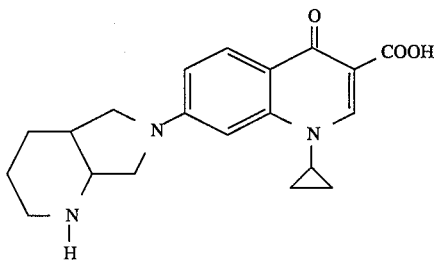

7-(2,8-Diazabicyclo[4.3.0]nonan-8-yl)-1-cyclopropyl-1,4-dihydro-4-oxo-3-quinolinecarboxylic acid 741 mg (3 mmol) of 1-cyclopropyl-7-fluoro-1,4-dihydro-4-oxo-3-quinolinecarboxylic acid together with 567 mg (4.5 mol) of 2,8-diazabicyclo[4.3.0]nonane and 672 mg of 1,4-diazabicyclo[2.2.2]octane are heated for two hours at 100° C. in 30 ml of N-methylpyrrolidone. The mixture is concentrated under a high vacuum, and the residue is stirred thoroughly with acetonitrile and dried at 100° C.

Yield: 820 mg (77% of theory) Melting point: 250°–252° C. (with decomposition)

EXAMPLE 2

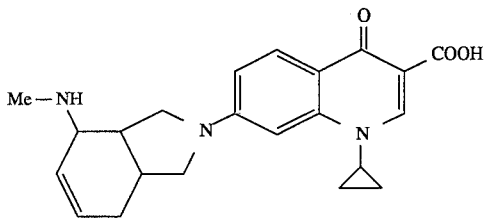

1-Cyclopropyl-1,4-dihydro-7-(4-methylamino-1,3,3a,4,7,7a-hexahydroisoindol-2-yl)-4-oxo-3-quinolinecarboxylic acid The title compound is obtained when 4-methylamino-1,3,3a,4,7,7a-hexahydroisoindole is reacted analogously to Example 1.

Melting point: 238°–240° C.

EXAMPLE 3

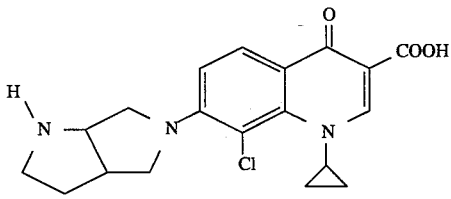

7-(2,7-Diazabicyclo[3.3.0]octan-7-yl)-8-chloro-1-cyclopropyl-1,4-dihydro-4-oxo-3-quinolinecarboxylic acid 650 mg (2.3 mmol) of 8-chloro-1-cyclopropyl-7-fluoro-1,4-dihydro-4-oxo-3-quinolinecarboxylic acid together with 315 mg (2.8 retool) of 2,7-diazabicyclo[3.3.0]octane and 510 mg (4.6 mmol) of 1,4-diazabicyclo[2.2.2]octane are heated for six hours at 120° C. in 23 ml of dimethyl sulphoxide. All volatile components are removed under a high vacuum, and the residue is stirred thoroughly with acetonitrile and dried at approximately 100° C.

Yield: 629 mg (72% of theory) Melting point: 202°–204° C. (with decomposition)

The following were prepared analogously to Example 3:

| Example | Z | Melting point [°C.] |
|---|---|---|
| 4 | (piperidine with NH and O, N—) | 250–255 |
| 5 | (piperidine with NH, N—) | 255–259 |
| 6 | HN—CH₃ (cyclohexene, N—) | 213–217 |
| 7 | NH₂ (cyclohexene, N—) | 184–186 (decomp.) |
| 8 | NH₂ (cyclohexene with Me, N—) | 169–171 (decomp.) |
| 9 | NH₂ (cyclohexene with CHMe₂, N—) | 145–147 (decomp.) |

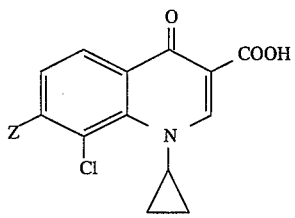

| Example | Z | Melting point [°C.] |
|---|---|---|
| 10 | Me—NH, Me, Me (substituted hexahydroisoindolyl) | 170–180 (decomp.) from acetonitrile |
| 11 | Me—NH, Me (substituted hexahydroisoindolyl) | 168–170 (decomp.) |
| 12 | OH-substituted hexahydroisoindolyl | 214–216 (decomp.) |
| 13 | NHMe-substituted hexahydroisoindolyl | 244–246 (decomp.) |
| 14 | NH₂, cyclopropyl-substituted hexahydroisoindolyl | 184–186 (decomp.) |

EXAMPLE 15

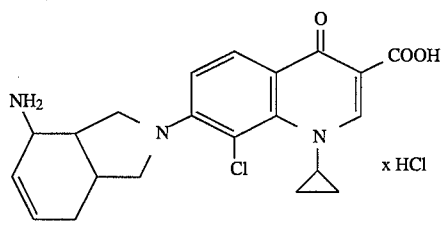

7-(4-Amino-1,3,3a,4,7,7a-hexahydroisoindol-2-yl)-8-chloro-1-cyclopropyl-1,4-dihydro-4-oxo-3-quinolinecarboxylic acid hydrochloride 2 g (5 mmol) of 7-(4-amino-1,3,3a,4,7,7a-hexahydroisoindol-2-yl)-3-chloro-1-cyclopropyl-1,4-dihydro-4-oxo-3-quinolinecarboxylic acid are stirred for 30 minutes at 60° C. in 60 ml of half-concentrated hydrochloric acid. Excess hydrochloric acid is removed in vacuo and the residue is stirred with acetonitrile.

Yield: 1.8 g (82% of theory) Melting point: 118°–120° C. (with decomposition)

EXAMPLE 16

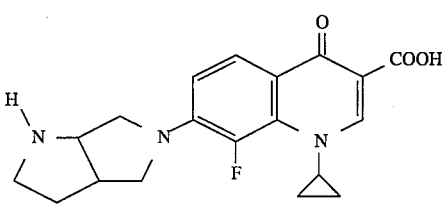

7-(2,7-Diazabicyclo[3.3.0]octan-7-yl)-1-cyclopropyl-8-fluoro-1,4-dihydro-4-oxo-3-quinolinecarboxylic acid 620 mg (2.3 mmol) of 1-cyclopropyl-7,8-difluoro-1,3-dihydro-4-oxo-3-quinolinecarboxylic acid together with 315 mg (2.8 mmol) of 2,7-diazabicyclo[3.3.0]octane and 0.51 g (4.6 mmol) of 1,4-diazabicyclo[2.2.2]octane are heated for two hours at 120° C. in 23 ml of dimethyl sulphoxide. All volatile components are removed under a high vacuum, and the residue is stirred thoroughly with acetonitrile and dried at approximately 100° C.

Yield: 770 mg (93% of theory) Melting point: 249°–251° C. (with decomposition)

The following were prepared analogously to Example 16:

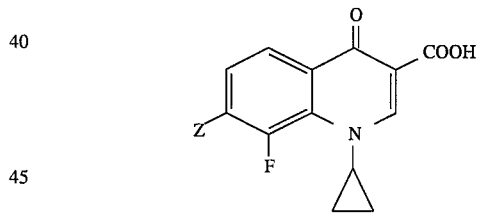

| Example | Z | Melting point [°C.] |
|---|---|---|
| 17 | 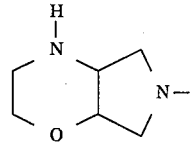 | 224–228 |
| 18 | piperidinyl-fused bicyclic amine with NH | 212–216 |
| 19 | 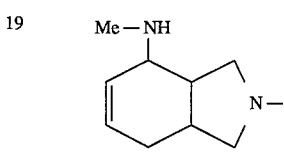 Me—NH-substituted hexahydroisoindolyl | 204–210 |

-continued

| Example | Z | Melting point [°C.] |
|---|---|---|
| 20 | 4-amino-hexahydroisoindol-2-yl | 158–160 (decomp.) |
| 21 | 4-amino-7-methyl-hexahydroisoindol-2-yl | 200–204 (decomp.) |
| 22 | 4-amino-7-isopropyl-hexahydroisoindol-2-yl | 250–252 (decomp.) |
| 23 | 4-methylamino-7-isopropyl-hexahydroisoindol-2-yl | 228–230 (decomp.) |
| 24 | 4-methylamino-7-methyl-hexahydroisoindol-2-yl | 191–193 (decomp.) |
| 25 | 4-hydroxymethyl-hexahydroisoindol-2-yl | 248–250 (decomp.) |
| 26 | 4-(methylaminomethyl)-hexahydroisoindol-2-yl | 168–170 (decomp.) |

-continued

| Example | Z | Melting point [°C.] |
|---|---|---|
| 27 | 4-amino-7-cyclopropyl-hexahydroisoindol-2-yl | 231–233 (decomp.) |

EXAMPLE b 28

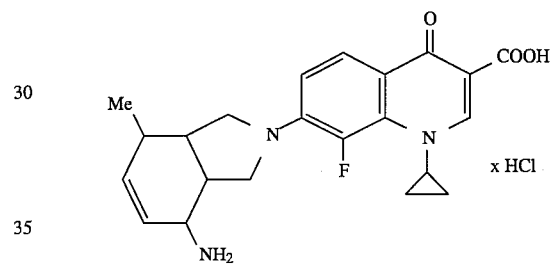

7-(4-Amino-7-methyl-1,3,3a,4,7,7a-hexahydroisoindol-2-yl)-1-cyclopropyl-8-fluoro-1,4-dihydro-4-oxo-3-quinolinecarboxylic acid hydrochloride The title compound is obtained when 7-(4-amino-7-methyl-1,3,3a,4,7,7a-hexahydroisoindol-2-yl)-1-cyclopropyl-8-fluoro-1,4-dihydro-4-oxo-3-quinolinecarboxylic acid is reacted analogously to Example 15.

Melting point: 262°–264° C. (with decomposition)

EXAMPLE 29

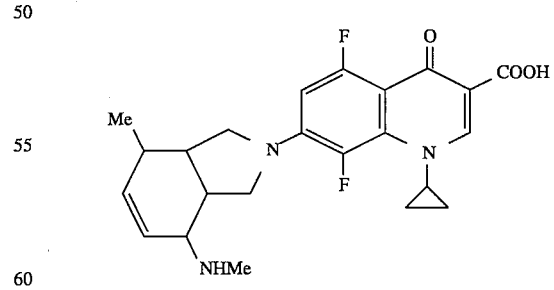

1-Cyclopropyl-5,8-difluoro-1,4-dihydro-7-(7-methyl-4-methylamino-1,2,3,3a,4,7,7a-hexahydroisoindol-2-yl)-4-oxo-3-quinolinecarboxylic acid 1.1 g (4 mmol) of 1-cyclopropyl-5,7,8-trifluoro-1,4-dihydro-4-oxo-3-quinolinecarboxylic acid together with 797 mg (4.8 mmol) of 7-methyl-4-methylamino-1,3,3a,4,7,7a-hexahydroisoindole and 896 mg (8 mmol) of 1,4-diazabicyclo[2.2.21]octane are stirred for two days at room temperature in 40 ml of dimethyl sulphoxide. All volatile components are removed under a high vacuum, and the residue is stirred with acetonitrile and dried at approximately 100° C.

Yield: 1.2 g (70% of theory) Melting point: 210°–212° C. (with decomposition)

EXAMPLE 30

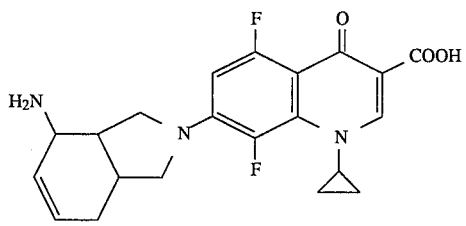

7-(4-Amino-1,3,3a,4,7,7a-hexahydroisoindol-2-yl)-1-cyclopropyl-5,8-difluoro-1,4-dihydro-4-oxo-3-quinolinecarboxylic acid The title compound is obtained when 4-amino-1,3,3a,4,7,7a-hexahydroisoindole is reacted analogously to Example 29.

Melting point: 272°–274° C. (with decomposition)

EXAMPLE 31

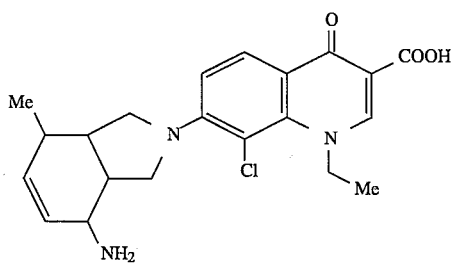

7-(4-Amino-7-methyl-1,3,3a,4,7,7a-hexahydroisoindol-2-yl)-8-chloro-1-ethyl-1,4-dihydro-4-oxo-3-quinolinecarboxylic acid 270 mg (1 mmol) of 8-chloro-1-ethyl-7-fluoro-1,4-dihydro-4-oxo-3-quinolinecarboxylic acid together with 180 mg (1.2 mmol) of 4-amino-7-methyl-1,3,3a,4,7,7a-hexahydroisoindole and 224 mg (2 mmol) of 1,4-diazabicyclo[2.2.2]octane are heated for three hours at 100° C. in 10 ml of dimethyl sulphoxide.

All volatile components are removed under a high vacuum, and the residue is stirred with acetonitrile and dried at 100° C.

Yield: 340 mg (85% of theory) Melting point: 164°–166° C.

EXAMPLE 32

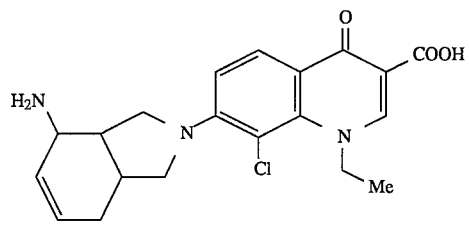

7-(4-Amino-1,3,3a,4,7,7a-hexahydroisoindol-2-yl)-8-chloro-1-ethyl-1,4-dihydro-4-oxo-3-quinolinecarboxylic acid The title compound is obtained when 4-amino-1,3,3a,4,7,7a-hexahydroisoindole is reacted analogously to Example 31.

Melting point: 194°–196° C. (with decomposition)

EXAMPLE 33

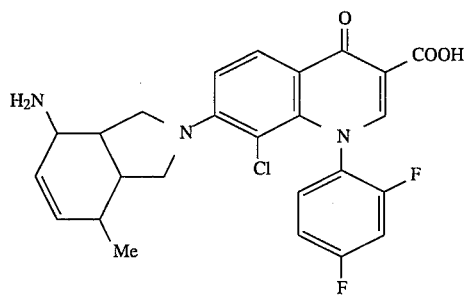

7-(4-Amino-7-methyl-1,3,3a,4,7,7a-hexahydroisoindol-2-yl)-8-chloro-1-(2,4-difluorophenyl)-1,4-dihydro-4-oxo-3-quinolinecarboxylic acid The title compound is obtained when 8-chloro-7-fluoro-1-(2,4-difluorophenyl)-1,4-dihydro-4-oxo-3-quinolinecarboxylic acid is reacted with 4-amino-7-methyl-1,3,3a,4,7,7a-hexahydroisoindole analogously to Example 31.

Melting point: 231°–233° C. (with decomposition)

EXAMPLE 34

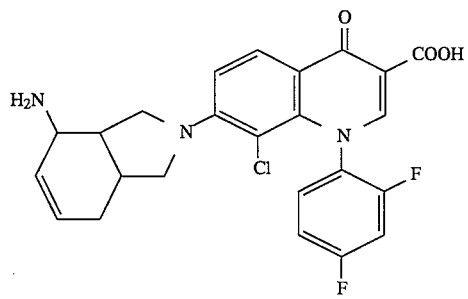

7-(4-Amino-1,3,3a,4,7,7a-hexahydroisoindol-2-yl)-8-chloro-1-(2,4-difluorophenyl)-1,4-dihydro-4-oxo-3-quinolinecarboxylic acid The title compound is obtained when 8-chloro-7-fluoro-1-(2,4-difluorophenyl)-1,4-dihydro-4-oxo-3-quinolinecarboxylic acid is reacted with 4-amino-1,3,3a,4,7,7a-hexahydroisoindole analogously to Example 31.

Melting point: 256°–258° C. (with decomposition)

EXAMPLE 35

7-(4-Amino-1,3,3a,4,7,7a-hexahydroisoindol-2-yl)-1-cyclopropyl-1,4-dihydro-4-oxo-1,8-naphthyridine-3-carboxylic acid hydrochloride

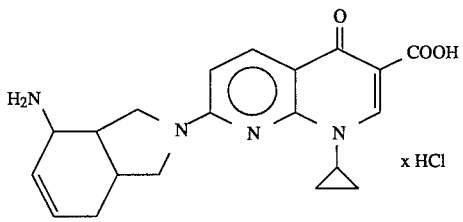

a) Ethyl 7-(4-amino-1,3,3a,4,7,7a-hexahydroisoindol-2-yl)-1-cyclopropyl-1,4-dihydro-4-oxo-1,8-naphthyridine-3-carboxylate 292 mg (1 mmol) of ethyl 7-chloro-1-cyclopropyl-1,4-dihydro-4-oxo-1,8-naphthyridine-3-carboxylate together with 0.3 g (2.2 mmol) of 4-amino-1,3,3a,4,7,7a-hexahydroisoindole are stirred for two hours under argon at room temperature in a mixture of 3 ml of dimethylformamide and 6 ml of acetonitrile. The solvents are removed under a high vacuum, and the residue is stirred with acetonitrile.

Yield: 160 mg (40% of theory) Melting point: 192°–193° C. (with decomposition)

7-(4-Amino-1,3,3a,4,7,7a-hexahydroisoindol-2-yl)-1-cyclopropyl-1,4-dihydro-4-oxo-1,8-naphthyridine-3-carboxylic acid hydrochloride 150 mg (0.38 mmol) of the ester obtained above are refluxed for ten hours in 4.2 ml of acetic acid and 3.4 ml of 18% strength hydrochloric acid. The mixture is evaporated to dryness on a rotary evaporator and the residue is dried at approximately 100° C.

Yield: 110 mg (73% of theory) Melting point: 268°–270° C. (decomposition)

EXAMPLE 36

7-(4-Amino-7-methyl-1,3,3a,4,7,7a-hexahydroisoindol-2-yl)-1-cyclopropyl-1,4-dihydro-4-oxo-1,8-naphthyridine-3-carboxylic acid hydrochloride

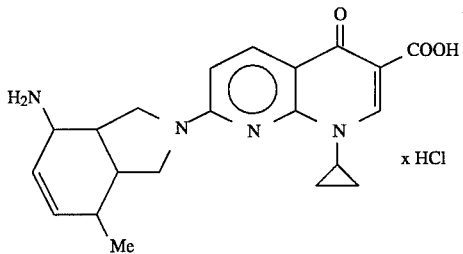

a) Ethyl 7-(4-amino-7-methyl-1,3,3a,4,7,7a-hexahydroisoindol- 2-yl)-1-cyclopropyl-1,4-dihydro-4-oxo-1,8-naphthyridine-3-carboxylate The title compound is obtained when 4-amino-7-methyl-1,3,3a,4,7,7a-hexahydroisoindole is reacted analogously to Example 35a.

Melting point: 172°–176° C.

b) 7-(4-Amino-7-methyl-1,3,3a,4,7,7a-hexahydroisoindol-2-yl)-1-cyclopropyl-1,4-dihydro-4-oxo-1,8-naphthyridine-3-carboxylic acid hydrochloride The title compound is obtained when the compound obtained above is reacted analogously to Example 35b.

Melting point: 260°–262° C.

EXAMPLE 37

7-(4-Amino-1,3,3a,4,7,7a-hexahydroisoindol-2-yl)-2,4-difluorophenyl-1,4-dihydro-4-oxo-1,8-naphthyridine-3-carboxylic acid hydrochloride

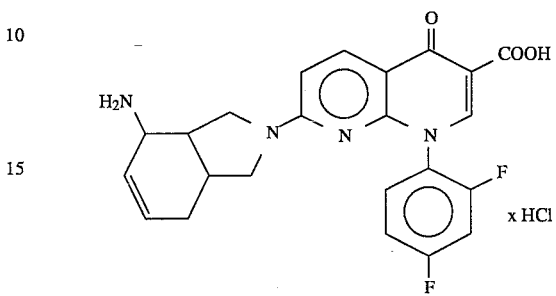

a) Ethyl 7-(4-amino-1,3,3a,4,7,7a-hexahydroisoindol-2-yl)-1-(2,4-difluorophenyl)-1,4-dihydro-4-oxo-1,8-naphthyridine-3-carboxylate The title compound is obtained when ethyl 7-chloro-1-(2,4-difluorophenyl)-1,4-dihydro-4-oxo-1,8-naphthyridine-3-carboxylate is reacted with 4-amino-1,3,3a,4,7,7a-hexahydroisoindole analogously to Example 35a.

Melting point: 178°–180° C.

b) 7-(4-Amino-1,3,3a,4,7,7a-hexahydroisoindol-2-yl)-1-(2,4-difluorophenyl)-1,4-dihydro-4-oxo-1,8-naphthyridine-3-carboxylic acid hydrochloride The title compound is obtained when the compound obtained above is reacted analogously to Example 35b.

Melting point: 254°–256° C.

EXAMPLE 38

7-(4-Amino-7-methyl-1,3,3a,4,7,7a-hexahydroisoindol-2-yl)-1-(2,4-difluorophenyl)-1,4 -dihydro-4-oxo-1,8-naphthyridine-3-carboxylic acid hydrochloride

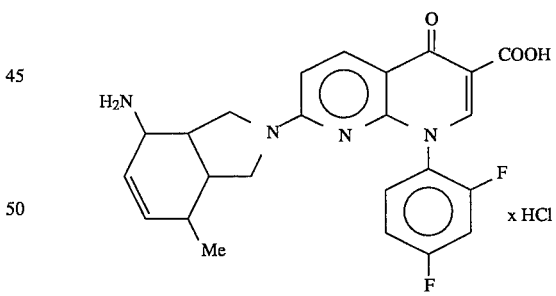

a) Ethyl 7-(4-amino-7-methyl-1,3,3a,4,7,7a-hexahydroisoindol-2-yl)-1-(2,4-difluorophenyl)-1,4-dihydro-4-oxo-1,8-naphthyridine-3-carboxylate The title compound is obtained when ethyl 7-chloro-1-(2,4-difluorophenyl)-1,4-dihydro-4-oxo-1,8-naphthyridine-3-carboxylate is reacted with 4-amino-7-methyl-1,3,3a,4,7,7a-hexahydroisoindole analogously to Example 35a.

Melting point: 143°–144° C.

b) 7-(4-Amino-7-methyl-1,3,3a,4,7,7a)-hexahydroisoindol-2-yl)-1-(2,4-difluorophenyl)-1,4-dihydro-4-oxo-1,8-naphthyridine-3-carboxylic acid hydrochloride The title compound is obtained when the compound obtained above is reacted analogously to Example 35b.

Melting point: 244°–245° C.

EXAMPLE 39

7-(4-Amino-1,3,3a,4,7,7a-hexahydroisoindol-2-yl)-8-chloro-1-(cis-2-fluorocyclopropyl)-1,4-dihydro-4-oxo-3-quinolinecarboxylic acid

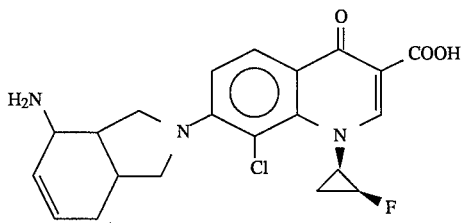

299 mg (1 mmol) of 8-chloro-7-fluoro-1-(cis-2-fluorocyclopropyl)-1,4-dihydro-4-oxo-3-quinolinecarboxylic acid together with 165 mg (1.2 mmol) of 4-amino-1,3,3a,4,7,7a-hexahydroisoindole and 224 mg (2 mmol) of 1,4-diazabicyclo[2.2.2]octane are stirred overnight at room temperature in 10 ml of dimethyl sulphoxide. All volatile components are removed under a high vacuum, and the residue is stirred with acetonitrile and dried at 100° C.

Yield: 400 mg (95% of theory) Melting point: 159°–161° C.

EXAMPLE 40

7-(4-Amino-7-methyl-1,3,3a,4,7,7a-hexahydroisoindol-2-yl)-8-chloro-1-(cis-2-fluorocyclopropyl)-1,4-dihydro-4-oxo-3-quinolinecarboxylic acid

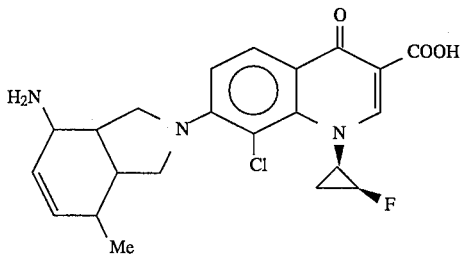

The title compound is obtained when 8-chloro-7-fluoro-1-(cis-2-fluorocyclopropyl)-1,4-dihydro-4-oxo-3-quinolinecarboxylic acid is reacted with 4-amino-7-methyl-1,3,3a,4,7,7a-hexahydroisoindole analogously to Example 39.

Melting point: 168°–170° C.

EXAMPLE 41

7-(4-Amino-1,3,3a,4,7,7a-hexahydroisoindol-2-yl)-8-chloro-1-(trans-2-fluorocyclopropyl)-1,4-dihydro-4-oxo-3-quinolinecarboxylic acid

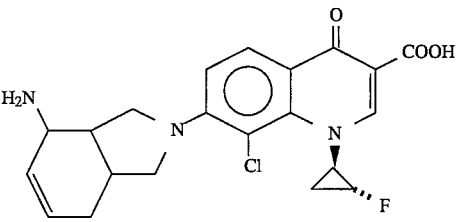

299 mg (1 mmol) of 8-chloro-7-fluoro-1-(trans-2-fluorocyclopropyl)-1,4-dihydro-4-oxo-3-quinolinecarboxylic acid together with 165 mg (1.2 mmol) of 4-amino-1,3,3a,4,7,7a-hexahydroisoindole and 224 mg (2 mmol) of 1,4-diazabicyclo[2.2.2]octane are stirred overnight at room temperature in 10 ml of dimethyl sulphoxide. All volatile components are removed under a high vacuum, and the residue is stirred with acetonitrile and dried at 100° C.

Yield: 400 mg (95% of theory) Melting point: 181°–183° C.

EXAMPLE 42

7-(4-Amino-7-methyl-1,3,3a,4,7,7a-hexahydroisoindol-2-yl)-8-chloro-1-(trans-2-fluorocyclopropyl)-1,4,-dihydro-4-oxo-3-quinolinecarboxylic acid

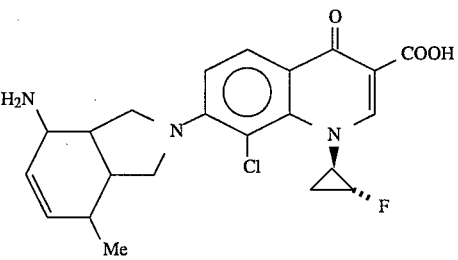

The title compound is obtained when 8-chloro-7-fluoro-1-(trans-2-fluorocyclopropyl)-1,4-dihydro-4-oxo-3-quinolinecarboxylic acid is reacted with 4-amino-7-methyl-1,3,3a,4,7,7a-hexahydroisoindole analogously to Example 41.

Melting point 177°–179° C.

EXAMPLE 43

7-(4-Amino-1,3,3a,4,7,7a-hexahydroisoindol-2-yl)-8-fluoro-1-(cis-2-fluorocyclopropyl)-1,4-dihydro-4-oxo-3-quinolinecarboxylic acid

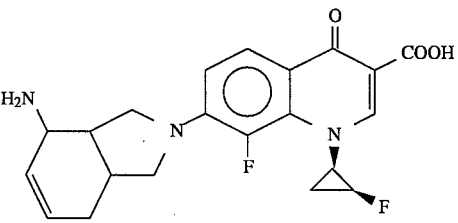

283 mg (1 mmol) of 7,8-difluoro-1-(cis-2-fluorocyclopropyl)-1,4-dihydro-4-oxo-3-quinolinecarboxylic acid together with 165 mg (1.2 mmol) of 4-amino-1,3,3a,4,7,7a-hexahydroisoindole and 224 mg (2 mmol) of 1,4-diazabicyclo[2.2.2]octane are stirred overnight at room temperature in 10 ml of dimethyl sulphoxide. All volatile components are removed under a high vacuum, and the residue is stirred with ethanol and dried at 100° C.

Yield: 330 mg (82% of theory) Melting point: 244°–246° C. (with decomposition)

EXAMPLE 44

7-(4-Amino-7-methyl-1,3,3a,4,7,7a-hexahydroisoindol-2-yl)-8-fluoro-1-(cis-2-fluorocyclopropyl)-1,4,-dihydro-4-oxo-3-quinolinecarboxylic acid

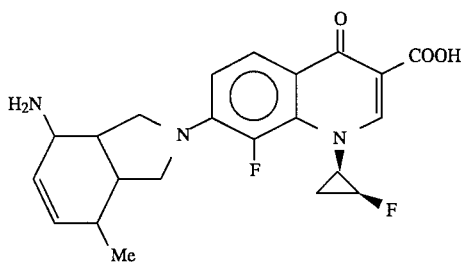

The title compound is obtained when 7,8-difluoro-1-(cis-2-fluorocyclopropyl)-1,4-dihydro-4-oxo-3-quinolinecarboxylic acid is reacted with 4-amino-7-methyl-1,3,3a,4,7,7a-hexahydroisoindole analogously to Example 43.

Melting point: 204°–206° C. (with decomposition)

EXAMPLE 45

7-(4-Amino-1,3,3a,4,7,7a-hexahydroisoindol-2-yl)-1-cyclopropyl-8-fluoro-5-trifluoromethyl-1,4-dihydro-4-oxo-3-quinolinecarboxylic acid

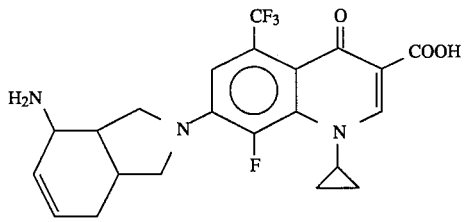

333 mg (1 mmol) of 1-cyclopropyl-7,8-difluoro-5-trifluoromethyl- 1,4-dihydro-4-oxo-3-quinolinecarboxylic acid together with 165 mg (1.2 mmol) of 4-amino-1,3,3a,4,7,7a-hexahydroisoindole and 224 mg (2 mmol) of 1,4-diazabicyclo[2.2.2]octane are stirred overnight at room temperature of dimethyl sulphoxide. All volatile components are removed under a high vacuum, and the residue is stirred with acetonitrile and dried at 100° C.

Yield: 330 mg (73% of theory) Melting point: 248°–249° C. (with decomposition)

EXAMPLE 46

7-(4-Amino-7-methyl-1,3,3a,4,7,7a-hexahydroisoindol-2-yl)-1-cyclopropyl-8-fluoro-5-trifluoromethyl-1,4-dihydro-4-oxo-3-quinolinecarboxylic acid

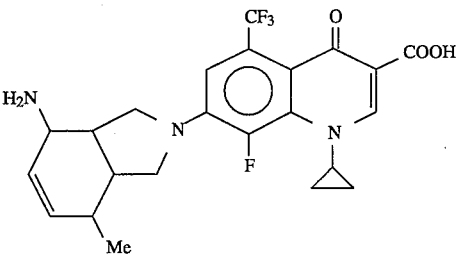

The title compound is obtained when 1-cyclopropyl-7,8-difluoro-5-trifluoromethyl-1,4-dihydro-4-oxo-3-quinolinecarboxylic acid is reacted with 4-amino-7-methyl-1,3,3a,4,7,7a-hexahydroisoindole analogously to Example 45.

Melting point: 242°–244° C. (with decomposition)

EXAMPLE 47

7-(4-Amino-1,3,3a,.4,7,7a-hexahydroisoindol-2-yl)-1-cyclopropyl-5-fluoro-8-trifluoromethyl-1,4-dihydro-4-oxo-3-quinolinecarboxylic acid

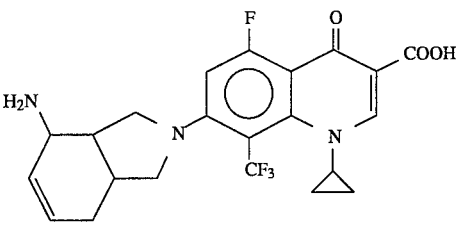

The title compound is obtained when 1-cyclopropyl-5,7-difluoro-8-trifluoromethyl-1,4-dihydro-4-oxo-3-quinolinecarboxylic acid is reacted with 4 -amino-1,3,3a,4,7,7a-hexahydroisoindole analogously to Example 45.

Melting point: 238°–240° C. (with decomposition)

EXAMPLE 48

7-(4-Amino-7-methyl-1,3,3a,4,7,7a-hexahydroisoindol-2-yl)-1-cyclopropyl-5-fluoro-8-trifluoromethyl-1,4-dihydro-4-oxo-3-quinolinecarboxylic acid

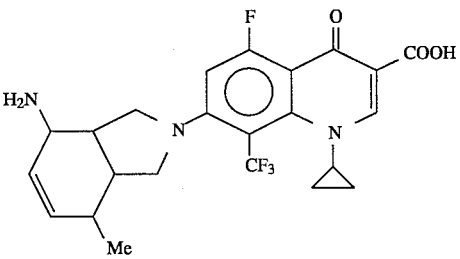

The title compound is obtained when 1-cyclopropyl-5,7-difluoro-8-trifluoromethyl-1,4-dihydro-4-oxo-3-quinolinecarboxylic acid is reacted with 4-amino-7-methyl-1,3,3a,4,7,7a-hexahydroisoindole analogously to Example 45.

Melting point: 234°–236° C. (with decomposition)

EXAMPLE 49

7-(4-Amino-7-methyl-1,3,3a,4,7,7a-hexahydroisoindol-2-yl)-1-cyclopropyl-8-trifluoromethyl-1,4-dihydro-4-oxo-3-quinolinecarboxylic acid

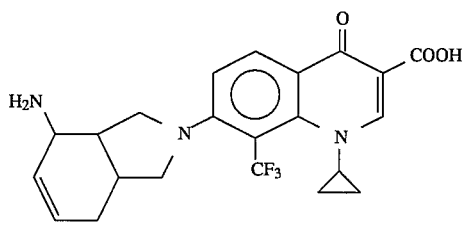

315 mg (1 mmol) of 1-cyclopropyl-7-fluoro-8-trifluoromethyl-1,4-dihydro-4-oxo-3-quinolinecarboxylic acid together with 165 mg (1.2 mmol) of 4-amino-1,3,3a,4,7,7a-hexahydroisoindole and 224 mg (2 mmol) of 1,4-diazabicyclo[2.2.2]octane are stirred for two hours at 100° C. in 10 ml of dimethyl sulphoxide. All volatile components are removed under a high vacuum, and the residue is stirred with acetonitrile and dried at 100° C.

Yield: 280 mg (65% of theory) Melting point: 168°–170° C. (with decomposition)

EXAMPLE 50

1-Cyclopropyl-5,8-difluoro-1,4-dihydro-7-(4-methylamino-1,2,3,3a,4,7,7a-hexahydroisoindol-2-yl)-4-oxo-3-quinolinecarboxylic acid

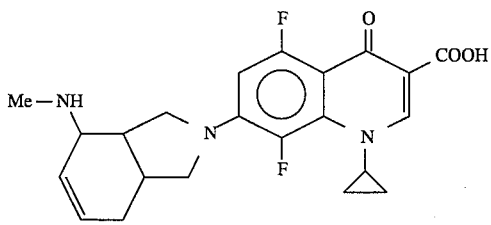

4.245 g (0.015 mol) of 1-cyclopropyl-5,7,8-trifluoro-1,4-dihydro-4-oxo-3-quinolinecarboxylic acid together with 2,736 g (0.018 mol) of 3-methylamino-1,3,3a,4,7,7a-hexahydroisoindole and 3.36 g (0.03 mol) of 1,4-diazabicyclo[2.2.21]octane are stirred overnight at room temperature in 150 ml of dimethyl sulphoxide. All volatile components are removed under a high vacuum, and the residue is stirred with acetonitrile.

Yield: 5.5 g (88% of theory) Melting point: 238°–240° C. (with decomposition)

EXAMPLE 51

5-Amino-1-cyclopropyl-8-fluoro-1,4-dihydro-7-(4-methylamino-1,3,3a,4,7,7a-hexahydroisoindol-2-yl)-4-oxo-3-quinolinecarboxylic acid

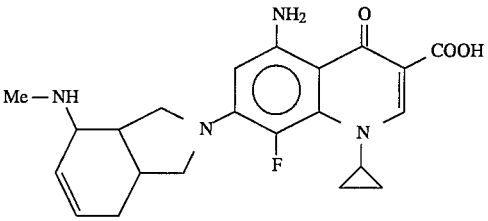

2 g (4.8 mmol) of 1-cyclopropyl-5,8-difluoro-1,4-dihydro-7-(4-methylamino-1,3,3a,4,7,7a-hexahydroisoindol-2-yl)-4-oxo-3-quinolinecarboxylic acid in 200 ml of dimethyl sulphoxide are introduced into an autoclave. After 5 ml of liquid ammonia have been added, the mixture is stirred for 9 hours at 140° C. and 6 bar. All volatile components are removed in vacuo, and the residue is stirred with ethanol.

Yield: 0.7 g (35.5% of theory) Melting point: 156°–158° C. (with decomposition)

We claim:

1. Quinolone- and naphthyridonecarboxylic acid derivatives of the formula (I)

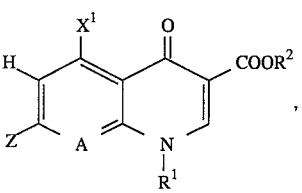

in which

R¹ represents straight-chain or branched $C_1$–$C_4$-alkyl which is optionally substituted by hydroxyl, halogen or $C_1$–$C_3$-alkoxy, $C_3$–$C_6$-cycloalkyl which is optionally substituted by $C_1$–$C_3$-alkyl or halogen, or $C_2$–$C_4$-alkenyl, furthermore $C_1$–$C_3$-alkoxy, amino, monoalkylamino having 1 to 3 C atoms, dialkylamino having 1 to 3 C atoms per alkyl group, or phenyl which is optionally monosubstituted to trisubstituted by halogen, R² represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)-methyl, X¹ represents hydrogen, halogen, amino, methyl or trifluoromethyl, Z represents radicals of the structures

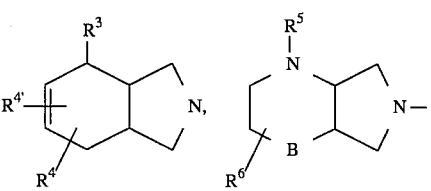

in which
$R^3$ represents hydrogen, hydroxyl, —$NR^7R^8$, hydroxymethyl or —$CH_2$—$NR^7R^8$, in which
$R^7$ denotes hydrogen, $C_1$-$C_3$-alkyl which is optionally substituted by hydroxyl, or denotes alkoxycarbonyl having 1 to 4 C atoms in the alkoxy moiety, or $C_1$-$C_3$-acyl and
$R^8$ denotes hydrogen or methyl,
$R^4$ represents hydrogen, straight-chain or branched $C_1$-$C_3$-alkyl or cyclopropyl,
$R^{4'}$ represents hydrogen or methyl,
$R^5$ represents hydrogen or methyl,
$R^6$ represents hydrogen, methyl or radicals of the structures —CH=CH—$CO_2R^{5'}$, —$CH_2$—$CH_2$—$CO_2R^{5'}$, —$CH_2$—CO—$CH_3$, —$CH_2$—$CH_2$—CN,
$R^{5'}$ represents methyl or ethyl,
B represents —$CH_2$—, O or a direct bond and
A represents N or C—$R^9$, in which
$R^9$ represents H, halogen, methyl, trifluoromethyl, vinyl, ethinyl, hydroxyl or methoxy,
in the form of racemates or as enantiomerically pure compounds, their pharmaceutically utilizable hydrates and acid addition salts and the alkali metal salts, alkaline earth metal salts, silver salts and guanidinium salts of the carboxylic acids on which they are based.

2. Quinolone- and naphthyridonecarboxylic acid derivatives according to claim 1, wherein
$R^1$ represents $C_1$-$C_2$-alkyl which is optionally substituted by hydroxyl or fluorine, $C_3$-$C_5$-cycloalkyl which is optionally substituted by fluorine, or vinyl, amino, monoalkylamino having 1 to 2 C atoms, dialkylamino having 1 to 2 C atoms per alkyl group, or phenyl which is optionally monosubstituted to disubstituted by halogen,
$R^2$ represents hydrogen, alkyl having 1 to 2 carbon atoms which is optionally substituted by amino or dimethylamino, or (5-methyl-2-oxo-1,3-dioxol-4-yl)-methyl,
$X^1$ represents hydrogen, fluorine, chlorine, trifluoromethyl or amino,
Z represents radicals of the structures

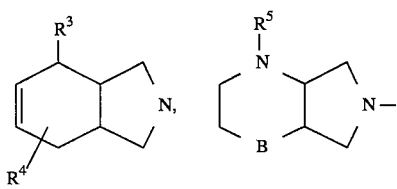

in which
$R^3$ represents hydrogen, hydroxyl, —$NR^7R^8$, hydroxymethyl or —$CH_2$—$NR^7R^8$, in which
$R^7$ denotes hydrogen, $C_1$-$C_2$-alkyl which is optionally substituted by hydroxyl, or denotes alkoxycarbonyl having 1 to 4 C atoms in the alkoxy moiety, or $C_1$-$C_3$-acyl and
$R^8$ denotes hydrogen or methyl,
$R^4$ represents hydrogen, straight-chain or branched $C_1$-$C_3$-alkyl or cyclopropyl,
$R^5$ represents hydrogen or methyl,
B represents —$CH_2$—, O or a direct bond and
A represents N or C—$R^9$, in which
$R^9$ represents H, chlorine, fluorine, methyl, trifluoromethyl, hydroxyl or methoxy.

3. Quinolone- and naphthyridonecarboxylic acid derivatives according to claim 1, wherein
$R^1$ represents methyl, ethyl, cyclopropyl which is optionally substituted by fluorine, or phenyl which is optionally monosubstituted or disubstituted by fluorine,
$R^2$ represents hydrogen, methyl or ethyl,
$X^1$ represents hydrogen, fluorine, trifluoromethyl or amino,
Z represents radicals of the structures

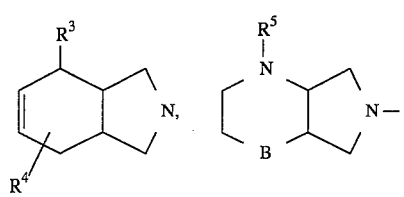

in which
$R^3$ represents hydrogen, hydroxyl, —$NR^7R^8$, hydroxymethyl or —$CH_2NR^7R^8$, in which
$R^7$ denotes hydrogen, methyl, alkoxycarbonyl having 1 to 4 C atoms in the alkoxy moiety, or $C_1$-$C_3$-acyl, and
$R^8$ denotes hydrogen or methyl,
$R^4$ represents hydrogen, straight-chain or branched $C_1$-$C_3$-alkyl or cyclopropyl,
$R^5$ represents hydrogen or methyl,
B represents —$CH_2$—, O or a direct bond and
A represents N or C—$R^9$, in which
$R^9$ represents H, chlorine, fluorine, methyl, methoxy, trifluoromethyl.

4. A method of combating a disease wherein an effective amount of a compound according to claim 1 is administered to a human or animal body.

5. A method of combating a bacterial infection wherein an effective amount of a compound according to claim 1 is administered.

6. A method of preserving inorganic or organic materials by adding thereto an effective amount of a compound according to claim 1.

7. An antibacterial composition comprising an antibacterially effective amount of a compound according to claim 1 and a diluent.

* * * * *